United States Patent [19]

Kawasaki et al.

[11] Patent Number: 5,470,569
[45] Date of Patent: Nov. 28, 1995

[54] RECOMBINANT COLONY STIMULATING FACTOR-1

[75] Inventors: Ernest S. Kawasaki, Richmond; Martha B. Ladner, Oakland; Janelle N. Van Arsdell, Richmond; Alice M. Wang, Lafayette; Peter Ralph, Orinda; Mazie Y. Coyne, Danville, all of Calif.; Mary K. Warren, Rockville, Md.

[73] Assignee: Cetus Oncology Corporation, Emeryville, Calif.

[21] Appl. No.: 212,300

[22] Filed: Mar. 14, 1994

Related U.S. Application Data

[63] Continuation of Ser. No. 794,822, Nov. 18, 1991, abandoned, which is a continuation of Ser. No. 358,394, May 26, 1989, abandoned, which is a division of Ser. No. 157,094, Feb. 9, 1988, Pat. No. 4,847,201, which is a continuation-in-part of Ser. No. 821,068, Jan. 21, 1986, abandoned, which is a continuation-in-part of Ser. No. 756,814, Jul. 18, 1985, abandoned, which is a continuation-in-part of Ser. No. 744,924, Jun. 14, 1985, abandoned, which is a continuation-in-part of Ser. No. 728,834, Apr. 30, 1985, abandoned, which is a continuation-in-part of Ser. No. 698,359, Feb. 5, 1985, abandoned.

[51] Int. Cl.$^6$ .................... A61K 38/19; C07K 14/535
[52] U.S. Cl. .................... 424/85.1; 530/351; 435/69.5
[58] Field of Search .................... 530/351, 395; 435/69.5; 930/145; 425/85.1

[56] References Cited

U.S. PATENT DOCUMENTS

| | | | |
|---|---|---|---|
| 4,230,697 | 10/1980 | Nishida et al. | 424/177 |
| 4,275,056 | 6/1981 | Takaku et al. | 424/99 |
| 4,342,828 | 8/1982 | Takaku et al. | 435/41 |
| 4,432,895 | 2/1984 | Tarnowski | 260/112 R |
| 4,438,032 | 3/1984 | Golde et al. | 260/112 R |
| 4,482,485 | 11/1984 | Funakoshi et al. | 260/112 R |
| 4,485,017 | 11/1984 | Tan et al. | 201/635 |
| 4,504,586 | 3/1985 | Nicolson | 436/518 |
| 4,658,018 | 4/1987 | Urdal et al. | 530/351 |
| 4,868,119 | 9/1989 | Clark et al. | 435/172.3 |
| 4,879,227 | 11/1989 | Clark et al. | 435/172.3 |
| 5,171,675 | 12/1992 | Arretti et al. | 435/69.5 |

FOREIGN PATENT DOCUMENTS

| | | |
|---|---|---|
| 0169566 | 1/1986 | European Pat. Off. . |
| 0249477 | 12/1987 | European Pat. Off. . |
| 0261592 | 3/1988 | European Pat. Off. . |
| 57-058629 | 4/1982 | Japan . |
| 60-041615 | 3/1985 | Japan . |
| 62-09323 | 4/1987 | Japan . |
| 2092159 | 8/1982 | United Kingdom . |
| 2134528 | 8/1984 | United Kingdom . |
| 8604607 | 8/1986 | WIPO . |
| 8604587 | 8/1986 | WIPO . |
| 8703204 | 6/1987 | WIPO . |
| 8706954 | 11/1987 | WIPO . |

OTHER PUBLICATIONS

Colony Stimulating Factor (Molecular and Cellular Biology), ed. Dexter et al, 1990, pp. 155–176.
Cerretti et al, *Molecular Immunol*, 1988, pp. 761–770, vol. 25(8).
Ralph et al, *Cellular Immunol*, 76, 1983, pp. 10–21.
Wang et al, *J. Cellular Biochem* 21, 1983, pp. 263–275.
Das et al *JBC* 257, 1982, pp. 13679–13684.
Ben Avram et al *PNAS* 82, 1985, pp. 4486–4489.
Zoller, et al., 1982, Nucleic Acids Research, 10(20):6487–6500.
Wells, et al., 1985, Gene, 34:315–323.

(List continued on next page.)

*Primary Examiner*—Garnette D. Draper
*Assistant Examiner*—Lorraine M. Spector
*Attorney, Agent, or Firm*—Philip L. McGarrigle; Lewis S. Gruber; Robert P. Blackburn

[57] ABSTRACT

A colony stimulating factor, CSF-1, is a lymphokine useful in overcoming the immunosuppression induced by chemotherapy or resulting from other causes. CSF-1 is obtained in usable amounts by recombinant methods, including cloning and expression of the murine and human DNA sequences encoding this protein.

8 Claims, 10 Drawing Sheets

OTHER PUBLICATIONS

Metcalf et al., 1986 *Blood* 67(2):257–267.
Clark et al., 1987 *Science* 236:1229–1237.
Dexter et al., 1984, *Nature* 309:746.
Kawasaki et al., 1985, *Science* 230:291–296.
Ladner et al., 1987 *EMBOJ* 6:(9):2693–2698.
Wong et al., 1987, *Science* 235:1504–1508.
DeLamarter et al., 1987, *Nucleic Acids Res.* 15(5):2389–2390.
Rajavashisth et al., 1987, *Proc. Natl. Acad. Sci. USA* 84:1157–1161.
Waheed et al., 1981, *Blood* 60:238–244.
Waheed et al., 1984 *Exp. Hematol.* 12:434.
Stanley, 1977, *J. Biol. Chem.* 252:4305–4312.
Das et al., 1981, *Blood* 58:630–641.
Stanley, 1985, *Meth. Enzymol.* 116:564–587.
Wu et al., 1979, *J. Biol. Chem.*254:6226–6228.
Wu et al., 1980, *Biochem.* 19:3846–3850.
Fojo et al., 1978, *Biochem.* 17:3109–3113.
Burgess et al., 1977, *J. Biol. Chem.* 252:1998–2003.
Csejtey et al., 1986, *Biochem. Biophys. Res. Comm.* 138:238–245.
Strickler et al., 1984, BIOSIS No. 28054134.
Kriegler et al., *Exp. Hematol.* 12:844–849 (1984).
Ben–Avram et al., 1985, *Proc. Natl. Acad. Sci. USA* 82:7801 (correction).
Biological Abstracts/RRM, vol. 5 No. 9, Abstract No. 29103717, 1985, *Genet. Technol. News (US)* Hester.
Biological Abstracts/RRM vol. 5, No. 15, Abstract No. 29077739, 1985 *Genet. Eng. Lett.* Fishbein.
Ishizaka et al., 1986, *Exp. Hematol* 14:1–8.
Motoyoshi et al., 1978 *Blood* 52:1012–1020.
Motoyoshi et al., 1983, Blood 62(3):685–688.
Warren et al., 1985, *J. Immunol.* 134(2):982–989.
Warren et al., 1986, *J. Immunol.* 137(7):2281–2285.
Ralph etal., 1986, *Immunobiol.* 172:194–204.
Vadas et al., 1983, *J. Immunol.* 130:793.
Nagata et al., 1986, *Nature* 319:415–418.
Nagata et al., 1986, *EMBOJ* 5(3):575–581.
Souza et al., 1986, *Science* 232:61–65.
Metcalf, 1985, *Science* 229:16–22.
Cantrell et al., 1985, *Proc. Natl. Acad. Sci. USA* 82:6250–6254.
Lusis et al., 1981, *Blood* 57:13–21.
Wong et al., 1985, *Science* 228:810–815.
Lee et al., 1985, *Proc. Natl. Acad. Sci. USA* 82:4360–4364.
Gough et al., 1984, *Nature* 309:763–767.
Fung et al., 1984, *Nature* 307:233–237.
Yokota et al., 1984, *Proc. Natl. Acad. Sci. USA* 81:1070–1074.

FIG.1a HUMAN N-TERMINAL:

AMINO ACID SEQUENCE OF CSF-1

```
 1                     5                          10                        15
Glu - Glu - Val - Ser - Glu - Tyr - Cys - Ser - His - Met - Ile - Gly - Ser - Gly - His
                       20                         25                        30
Leu - Gln - Ser - Leu - Gln - Arg - Leu - Ile - Asp - Ser - Gln - Met - Glu - Thr - Ser
                       35                         40
Cys - Gln - Ile - Thr - Phe - Glu - Phe - Val - Asp - Gln - Glu - Gln - Leu - Val
```

FIG. 1a

FIG.1b MURINE N-TERMINAL:

```
 1                     5                          10                        15
Lys - Glu - Val - Ser - Glu - His - Cys - Ser - His - Met - Ile - Gly - Asn - Gly - His
                       20                         25                        30
Leu - Lys - Val - Leu - Gln - Gln - Leu - Ile - Asp - Ser - Gln - Met - Glu - Thr - Ser
                                        35
(Tyr)-(Gln)-(Ile)-(Ala)-(Phe)-(Glu)- X  -(Val)-(Thr)
```

FIG. 1b

FIG.1c MURINE INTERNAL CYANOGEN BROMIDE-CLEAVAGE PEPTIDE:

```
 1                     5                          10                        15
(Met) - Glu - Phe - Lys - Asp - Asn -(Thr)- Pro - Asn - Ala - Phe - Ala - Asx - Glu -(Arg)- Leu
                             20
Gln - Glu -(Asp)-(Ser)-(Asn)-(Asn)-(Leu)-(Asn)
```

FIG. 1c

PROBES FOR MURINE CSF

```
              5   6   7   8   9
              Glu-His-Cys-Ser-His

CODING        GAACATTGT /TCA \CA
SEQUENCE         G   C  C(  T  )
                        (  G  )
                        \  C  /

OR

/AGT\
                      \ C /
```

REGION B

```
REVERSE       TG/AGA\ACAATGTTC
COMPLEMENT      ( T )G  G   C
                ( G )
                \ C /

OR

/ACT\
                  \ G /
```

```
              9   10  11  12  13
              His-Met-Ile-Gly-Asn

CODING        CATATGATTGGAAAT
SEQUENCE         C     C T  C
                       A G
                         C
```

REGION A

```
REVERSE       ATTACCAATCATATG
COMPLEMENT       G  T G    G
                      G
                      C
```

FIG. 2

HUMAN CSF AA SEQUENCE- & OLIGOS

NH₂+

GLU GLU VAL SER GLU TYR CYS SER HIS MET ILE GLY

5'+
```
GAG GAG GTG TCC GAG TAC TGC TCC CAC ATG ATC GGC
 A   A   C   T   A   T   T   T   T           T   G
         T       A           A               A   T
         A       G           G                   A
             AGC                 AGC
              T                   T
```

EK12
```
CC GAT CAT GTG GGA GCA GTA CTC
 A       A       A       T
```

EK13
```
CC GAT CAT GTG GCT GCA GTA CTC
 A       A       A   A   T
```

EK14
```
CC GAT CAT GTG GGA GCA GTA CTC GGA CAC CTC CTC
                CT                  CT
```

EK15
```
GAG TAC TGC TCC CAC ATG
 A   T   T  AG   T
```

EK18
```
GAG GAG GTG TCC GAG TAC
 A   A   C  AG   A   T
```

EK21
```
GTA CTC GGA CAC CTC CTC
 A   T   A   G   T   T
```

EK22
```
GTA CTC GCT CAC CTC CTC
 A   T   A   G   T   T
```

EK23
```
GAG TAC TGC TCC CAC ATG ATC GG
 A   T   T   T   T       T
             A
             G
```

EK24
```
GAG TAC TGC AGC CAC ATG ATC GG
 A   T   T   T   T       T
```

FIG. 3

PARTIAL HUMAN CSF-1 SEQUENCE

```
  1 GAAGGTGACATCTGGGCTGTTTTCATGGGAGAACAAGGTTGTGCTGTGGCTGCTAGAAAT
 61 CCTGGGAAAGCTGGATTTGAGGGATGCTGTATCCTGAGGTAAGGGCAGAGCCTGTAGCAT
121 TGTAGATATGAGGCCTTTGTTTTTCTGCGTTGAGCAGGGCATGGGGATAACTGGGGAGAG
181 TGAGACCTGGGGAGAAATGACACCCTCTCTGTCACAGACATGGCTGGGCTCCCTGCTGTT
                                        ThrTrpLeuGlySerLeuLeuLeu
241 GTTGGTCTGTCTCCTGGCGAGCAGGAGTATCACCGAGGAGGTGTCGGAGTACTGTAGCCA
    LeuValCysLeuLeuAlaSerArgSerIleThrGluGluValSerGluTyrCysSerHis
                                      *  *  *  *  *  *  *
301 CATGATTGGGAGTGGACACCTGCAGTCTCTGCAGCGGCTGGTGAGTGTGTGGCCATGCTG
    METIleGlySerGlyHisLeuGlnSerLeuGlnArgLeu
     *  *  *  *  *  *  *  *  *  *  *
361 TATTCTACCTTCTCCCCACTGGGGAAATGAAGGCAGGAGCCAGGGAGCAGGTCAAAGAGA
421 GCAGTTGCAGGCAGGAAAATAGGGCAGTGCGGGACATTGCTTGTGGTTCCCACTAGCTCC
481 ACCAGTGATACCCTTCACTAACCTTCCCAAAGTTAGGACCTCTGGTCTCCCCAGCTCGAA
541 GCCCTCTCTGACTGCCCTGCAGGCAGTGGATGCTGTGGGCTTCCAGCTGCTTGCCTGGGT
601 TAGTGATTGCCCAGGAACATCAACCACTGATTCTGAAAAGGCTTCTGAGGTCTGCTGTCC
661 CTCAGTGGGATGCCTCCTCTGGGAAGCTAGCCCAGGCGGCCTGCTGTGTCCAGATGTTGC
```

FIG. 4a

721 ATCTAGCCTCCTGGACTCTCATATGTGGCGCAGTCTGCGATCAGAGCCCCACCAGATTTG
781 GAGGGAAGCGCTTGCCTAACTCCAGCCTTCCACACTCACTT . . . 200 BASES . .
. . .TCCAGGGCCCTGAGCTTGGGGCCTGTGGGCTGTGCCTTCCGCCTCTCTTGCCCCAGCACT
 61 ACTTCTCCTGTATGTAGTTGCTGTAGCAATCCAAGGTAGACCAAGAGCCCCAGCATTCTC
121 TGAGGCTTAAAATCCAGAACTGCTGCTCTGGGGCTAAAGAGGGCTTTAAGGGCATCCAGC
181 TCCAACCCCTACAGGTGTTCAATCCCCAGAGCTTGTCCAGCCTCTGCTTGAATTCCTACC
241 ATGACAGGGTGCTCACTGCCTCCAGGGAAGATTATATCCTATATTCTTCTATAGACATCT
301 CTTCCTTAAAACAAATGGGCATTTGTCAGATTTCGTGGGGTGGTAGAAGGAAAGAAGAGA
361 CTTCTTGTTCTTCTACAGCCTTCCCCTGGGCATCTGGAAGGCACTGATCTTCTCCTAGAC
421 TTGACTCTGTCTTTCCACGTGTGGTTGGCAGGGATGAAGTTCAAACCCCAATCCACTCAG
481 AAGCTAAGGTCCCCGTTTTGAAGAAGGCTGAAGGCTGAGTTGAGCTGTAGGTTACCCTGC
541 AATCGTTGGCCTGCTCTCTCTTACAGATTGACAGTCAGATGGAGACCTCGTGCCAAATTA
                              IleAspSerGlnMETGluThrSerCysGlnIleThr
                               *   *   *   *   *   *   *   *   *
601 CATTTGAGTTTGTAGACCAGGAACAGTTGGTGAGTGATGGCTTTTTACAAAATCCATGCA
    PheGluPheValAspGlnGluGlnLeu
     *   *   *   *

FIG. 4b

661  CCAGCCTGCATGCAACTCCCAGGGTGGGGTGTGTGGGGGAGCATGAAAGCGGCAGAATGC
721  CTACTGCTGGAAAGGGTGAGAGTGTGAGGATCCATGGGTGCTCAACTCTGGGGTGCCAGG
781  ATCCAGGGCTCAAGTCCCCTGCCATTCCCTTCTCCTGGCCTGATACATAACAAGCGCTCA
841  CTAGGTACCAAGCACTTTGCTAATGTAGTTCTGACAGTACCACTATGTGGTACACAAATA
901  CAGTTTATTATCCACAGAGAGGTGAAAGGAGCATAGCTAGTAGGTGCTAGAGGCCTGATT
961  TGAATCCAGGAAGGTTGGCTGTAGGGCTTGAGGCAAATCAATACTTCTTCCAGGTCACAA
1021 GCTT

\* DENOTES MATCH TO MURINE AMINO ACID SEQUENCE
— DENOTES MATCH TO HUMAN AMINO ACID SEQUENCE
↓ DENOTES INTRON/EXON BOUNDARY

FIG. 4c

```
                                                                                        120
                        20                    40                    60             80                           100
AGTGAGGCTC GGCCCGGGGA AAGTGAAAGT TTGCCTGGGT CCTCTCGGCG CCAGAGCCGC TCTCCGCATC CCAGGACAGC GGTGCGGCCC TCGGCCGGGG CGCCCACTCC GCAGCAGCCA
                        140                   160                                      180                      200                       220
GCGAGCGAGC GAGCGAGCGA GGGCGGCCGA CGCGCCGGGC GGGACCCAGC TGCCCGT    ATG ACC GCG CCG GGC GCC GCC CGC CCT CCC ACG TGG CTG GGC
                                                                  Met Thr Ala Pro Gly Ala Ala Arg Cys Pro Pro Thr Trp Leu Gly
                                                                  -32
            240                   260                   280                       300                       320
TCC CTG CTG TTG GTC TGT CTC CTG GCG AGC AGG AGT ATC ACC GAG TAC TGT TCG GAG TAC TGT AGC CAC ATG ATT GGG AGT GGA CAC CTG CAG TCT
Ser Leu Leu Leu Val Cys Leu Leu Ala Ser Arg Ser Ile Thr Glu Tyr Cys Ser Glu Tyr Cys Ser His Met Ile Gly Ser Gly His Leu Gln Ser
                                                                                                                10
        340                   360                       380                       400                       420
CTG CAG CGG ATT GAC AGT CAG ATG GAG ACC TCG TGC CAA ATT ACA TTT GAG TTT GTA GAC GAG CAG TTG AAA GAT CCA GTG TGC TAC CTT AAG
Leu Gln Arg Ile Asp Ser Gln Met Glu Thr Ser Cys Gln Ile Thr Phe Glu Phe Val Asp Glu Gln Leu Lys Asp Pro Val Cys Tyr Leu Lys
    20                                                            30                         40
            440                       460                       480                           500                       520
AAG GCA TTT CTC CTG GTA CAA TAC ATA ATG GAG GAC ATG GAG AAC CCC AAT ATT GCC ATT GTG CAG CTG CAG GAA CTC TCT
Lys Ala Phe Leu Leu Val Gln Tyr Ile Met Glu Asp Met Glu Asn Pro Asn Ile Ala Ile Val Gln Leu Gln Glu Leu Ser
                            60                                                                    80
        540                       560                       580                       600                       620
TTG AGG AGC AAG TGC TTC TTC ACC AAG GAT TAT GAA GAT CAT GAG GCC ACA CCT GAG TAT CTC CAG TTG CTG GAG AAG GTC
Leu Arg Ser Lys Cys Phe Phe Thr Lys Asp Tyr Glu Asp His Glu Ala Thr Pro Glu Tyr Leu Gln Leu Leu Glu Lys Val
                                                100
            640                       660                       680                       700                       720
AAG AAT GTC TTT AAT GAA ACA AAG AAT CTC CTT GAC AAG GAC TGG AAT ATT TTC AGC AAG AAC TGC AAC AGC TTT GCT GAA AGC TGC CTC
Lys Asn Val Phe Asn Glu Thr Lys Asn Leu Leu Asp Lys Asp Trp Asn Ile Phe Ser Lys Asn Cys Asn Ser Phe Ala Glu Ser Cys Leu
            120                                                       140
```

FIG. 5a

```
                740              760              780              800              820
CAT GAG AGG CAG TCC GAG GGA TCC TCC AGC CCG CAG CTC CAG GAG TCT GTC TTC CAC CTG CTG GTG CCC AGT GTC ATC CTG GTC TTG CTG GCC GTC GGA
His Glu Arg Gln Ser Glu Gly Ser Ser Ser Pro Gln Leu Gln Glu Ser Val Phe His Leu Leu Val Pro Ser Val Ile Leu Val Leu Leu Ala Val Gly
                                              160                                                                         180
                840              860              880              900              920
GGC CTC TTG TTC TAC AGG TGG AGG CGG AGC CAT CAA GAG GCG GAT TCT CCC TTG GAG CAA CCA GAG GGC AGC CCC TGG ACT CAG GAT
Gly Leu Leu Phe Tyr Arg Trp Arg Arg Ser His Gln Glu Ala Asp Ser Pro Leu Glu Gln Pro Glu Gly Ser Pro Leu Thr Gln Asp
                                              200
                940              960              980              1000             1020
GAC AGA CAG GAA CTG GAA CTG CCA GTG TAG AGGGAATTCTAA GACCCCTCAC CATCCTGGAC ACACTCGTTT GTCAATGTCC CTCTGAAAAT GTGACGCCCA GCCCCGGACA
Asp Arg Gln Glu Leu Glu Leu Pro Val
            220
     1040          1060          1080          1100          1120          1140
CAGTACTCCA GATGTTGTCT GACCAGCTCA GAGAGAGTAC AGTGGGACTG TTACCTTCCT TGATATGGAC AGTATTCTTC TATTGTGCA GATTAAGATT GCATTAGTTT TTTTCTTAAC
     1160          1180          1200          1220          1240          1260
AACTGCATCA TACTGTTGTC ATATGTTGAG CCTGTGGTCT ATTAAAACCC CTAGTTCCAT CTTCTGTCAA GCCAGACCAT CTCTACCCTG TACTTGGACA ACTTAACTTT
     1280          1300          1320          1340          1360          1380
TTTAACCAAA GTGCAGTTTA TGTTCACCTT TGTTAAAGCC ACCTTGTGGT TTCTGCCCAT CACCTGAACC TACTGAAGTT GTGTGAAATC CTAATTCTGT CATCTCCGTA GCCCTCCAG
     1400          1420          1440          1460          1480          1500
TTGTGCCTCC TGCACATTGA TGAGTGCCTG CTGTTGTCTT GCCCATGTT GTTGATGTAG CTGTGACCCT ATTGTTCCTC ACCCTGCCC CCCGCCAACC CCAGTGCC CACCTCTTCC
     1520          1540          1560          1580          1600          1620
CCCTCCCACC CAAGCCCACA GCCAGCCCAT CAGGAAGCCT TCCTGGCTTC TCCACAACCT TCTGACTGCT CTTTTCAGTC ATGCCCCTCC TGCTCTTTTG TATTTGGCTA ATAGTATATC
     1640
AATTTGCACT T
```

FIG.5b

RECOMBINANT COLONY STIMULATING FACTOR-1

CROSS-REFERENCE TO RELATED APPLICATION

This is a continuation of U.S. application Ser. No. 07/794,822, filed Nov. 18, 1991, now abandoned, which is a continuation of application Ser. No. 07/358,394, filed May 26, 1989, now abandoned, which is a division of application Ser. No. 157,094, filed Feb. 9, 1988 issued Jul. 11, 1989 as U.S. Pat. No. 4,847,201, which is a continuation-in-part of U.S. patent application Ser. No. 821,068, filed 21 Jan. 1986, now abandoned, which is a continuation-in-part of U.S. patent application Ser. No. 756,814, filed 18 Jul. 1985, now abandoned, which is a continuation-in-part of U.S. patent application Ser. No. 744,924, filed 14 Jun. 1985, now abandoned, which is a continuation-in-part of U.S. patent application Ser. No. 728,834, filed 30 Apr. 1985, now abandoned, which is a continuation-in-part of U.S. Ser. No. 698,359, filed 5 Feb. 1985 now abandoned.

TECHNICAL FIELD

The present invention relates to the use of recombinant technology for production of lymphokines ordinarily produced in low concentration. More specifically, the invention relates to the cloning and expression of a DNA sequence encoding human colony stimulating factor-1 (CSF-1).

BACKGROUND ART

The ability of certain factors produced in very low concentration in a variety of tissues to stimulate the growth and development of bone marrow progenitor cells into granulocytes and/or macrophages has been known for nearly 15 years. The presence of such factors in sera, urine samples, and tissue extracts from a number of species is demonstrable using an in vitro assay which measures the stimulation of colony formation by bone marrow cells plated in semi-solid culture medium. There is no known in vivo assay. Because these factors induce the formation of such colonies, the factors collectively have been called Colony Stimulating Factors (CSF).

More recently, it has been shown that there are at least four subclasses of human CSF proteins which can be defined according to the types of cells found in the resultant colonies. One subclass, CSF-1, results in colonies containing macrophages predominantly. Other subclasses produce colonies which contain both neutrophilic granulocytes and macrophages; which contain predominantly neutrophilic granulocytes; and which contain neutrophilic and eosinophilic granulocytes and macrophages.

There are murine factors analogous to the first three of the above human CSFs. In addition, a murine factor called IL-3 induces colonies from murine bone marrow cells which contain all these cell types plus megakaryocytes, erythrocytes, and mast cells, in various combinations. These CSFs have been reviewed by Dexter, T. M., *Nature* (1984) 309:746, and Vadas, M. A., et al, *J Immunol* (1983) 130:793.

The invention herein is concerned with the recombinant production of proteins which are members of the first of these subclasses, CSF-1. This subclass has been further characterized and delineated by specific radioimmunoassays and radioreceptor assays—e.g., antibodies raised against purified CSF-1 are able to suppress specifically CSF-1 activity, without affecting the biological activities of the other subclasses, and macrophage cell line J774 contains receptors which bind CSF-1 specifically. A description of these assays was published by Das, S. K., et al, *Blood* (1981) 58:630.

Purification methods for various CSF proteins have been published and are described in the following paragraphs.

Stanley, E. R., et al, *J Biol Chem* (1977) 252:4305 reported purification of a CSF protein from murine L929 cells to a specific activity of about $1\times10^8$ units/mg, which also stimulated mainly macrophage production. Waheed, A., et al, *Blood* (1982) 60:238, described the purification of mouse L-cell CSF-1 to apparent homogeneity using a rabbit antibody column and reported the first 25 amino acids of the murine sequence (Ben-Avram, C. M., et al, *Proc Natl Acad Sci (USA)* (1985) 882:4486).

Stanley, E. R., et al, *J Biol Chem* (1977) 252:4305–4312 disclosed a purification procedure for CSF-1 from human urine and Das, S. K., et al, *Blood* (1981) 58:630; *J Biol Chem* (1982) 257:13679 obtained a human urinary CSF-1 at a specific activity of $5\times10^7$ units/mg which produced only macrophage colonies, and outlined the relationship of glycosylation of the CSF-1 proteins prepared from cultured mouse L-cells and from human urine to their activities. Wang, F. F., et al, *J Cell Biochem* (1983) 21:263, isolated human urinary CSF-1 to specific activity of $10^8$ U/mg. Waheed, A., et al, disclosed purification of human urinary CSF-1 to a specific activity of $0.7–2.3\times10^7$ U/mg on a rabbit antibody column (*Exp Hemat* (1984) 12:434).

Wu, M., et al, *J Biol Chem* (1979) 254:6226 reported the preparation of a CSF protein from cultured human pancreatic carcinoma (MIAPaCa) cells which resulted in the growth of murine granulocytic and macrophagic colonies. The resulting protein had a specific activity of approximately $7\times10^7$ units/rag.

Partially purified preparations of various CSFs have also been reported from human and mouse lung-cell conditioned media (Fojo, S. S., et al, *Biochemistry* (1978) 17:3109; Burgess, A. W., et al, *J Biol Chem* (1977) 252:1998); from human T-lymphoblast cells (Lusis, A. J., et al, *Blood* (1981) 57:13: U.S. Pat. No. 4,438,032); from human placental conditioned medium to apparent homogeneity and specific activity of $7\times10^7$ U/mg (Wu, M., et al, *Biochemistry* (1980) 19:3846).

A significant difficulty in putting CSF proteins in general, and CSF-1 in particular, to any useful function has been their unavailability in distinct and characterizable form in sufficient amounts to make their employment in therapeutic use practical or even possible. The present invention remedies these deficiencies by providing purified human and murine CSF-1 in useful amounts through recombinant techniques.

A CSF protein of a different subclass, murine and human GM-CSF has been purified and the cDNAs cloned. This protein was shown to be distinct from other CSFs, e.g., CSF-1, by Gough, et al, *Nature* (1984) 309:763–767. Murine IL-3 has been cloned by Fung, M. C., et al, *Nature* (1984) 307:233. See also Yokota, T., et al, *PNAS* (1984) 81:1070–1074; Wong, G. G., et al, *Science* (1985) 228:810–815; Lee, F., et al, *PNAS* (1985) 82:4360–4364; and Cantrell, M. A., et al, *PNAS* (1985) 82:6250–6254.

DISCLOSURE OF THE INVENTION

In one aspect, the present invention relates to recombinant CSF-1 protein, including the biologically active proteins containing modifications of primary amino acid sequence of the native protein. CSF-1 protein in recombinant form can be obtained in quantity, can be modified advantageously through regulation of the post-translational processing provided by the host, and can be intentionally modified at the genetic or protein level to enhance its desirable properties. For example, muteins having deletions of substantial portions of the carboxy terminal one-third of the polypeptide are thus active. Thus, the availability of CSF-1 in recombinant form provides both flexibility and certain quantitative advantages which make possible applications for use of the protein therapeutically, that are unavailable with respect to the native protein.

In other aspects, the invention relates to an isolated DNA sequence encoding recombinant CSF-1, to recombinant expression systems for this sequence and to vectors containing them, to recombinant hosts which are transformed with these vectors, and to cultures producing the recombinant protein. The invention further relates to methods for producing the recombinant protein and to the materials significant in its production.

In addition, the invention relates to compositions containing CSF-1 which are useful in pharmaceutical and therapeutic applications, and to methods of use for such compositions.

BRIEF DESCRIPTION OF THE DRAWINGS

FIGS. 1A through 1C show the partial amino acid sequences of human urinary and murine L-929 cell CSF-1 as determined from purified native proteins.

FIG. 2 shows the sequence of certain oligomer probes for murine CSF-1.

FIG. 3 shows the sequence of oligomer probes used to obtain human genomic CSF-1.

FIGS. 4A through 4C show the sequenced portion of a 3.9 kb HindIII fragment encoding human CSF-1 sequences and the deduced amino acid sequences for the exon regions.

FIGS. 5A and 5B show the DNA and deduced amino acid sequences for a cDNA clone encoding CSF-1.

MODES FOR CARRYING OUT THE INVENTION

A. Definitions

Figure 6:
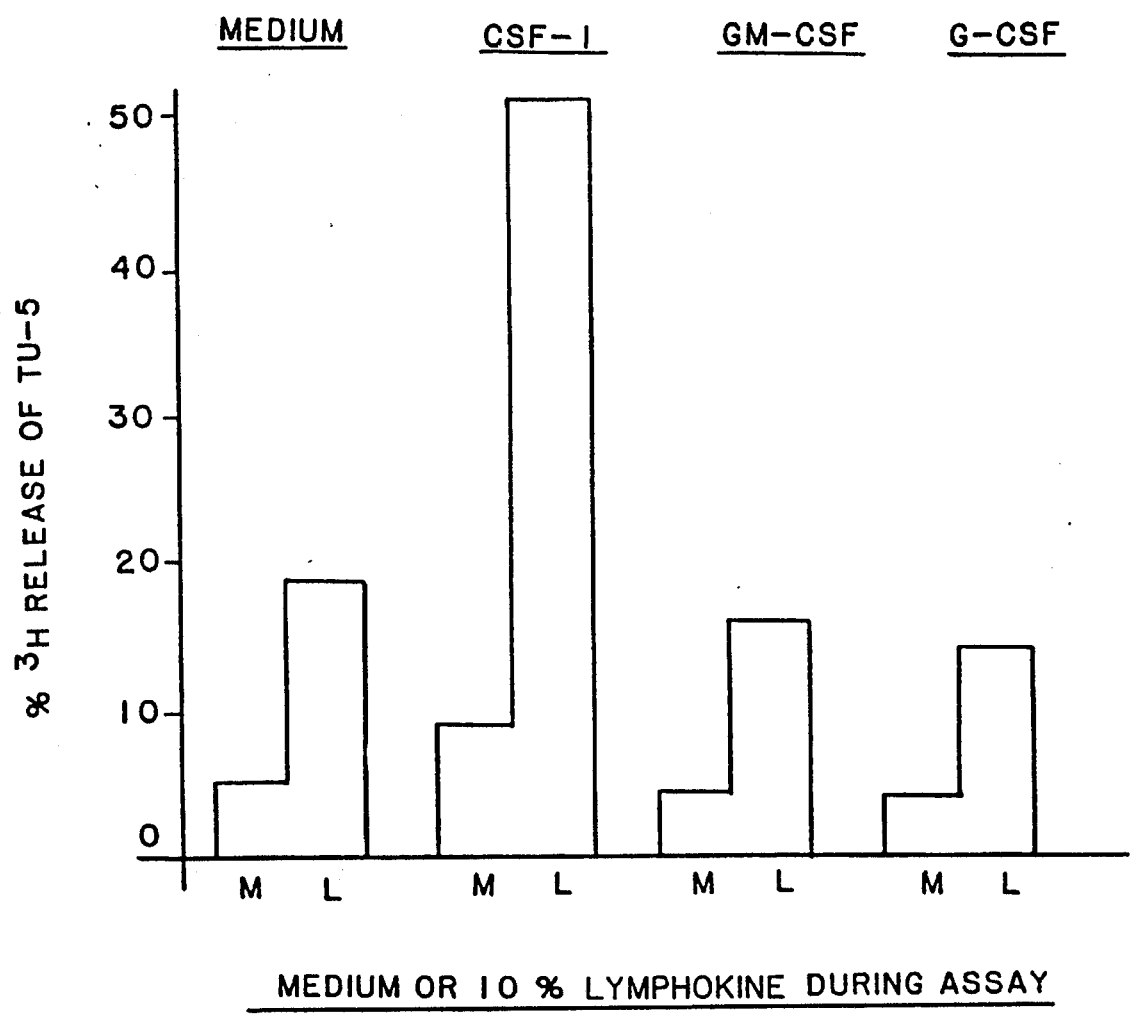
FIG. 6 shows a comparison of the activities of CSF-1 and other colony stimulating factors in enhancing the ability of macrophages to kill tumor cells.

"Colony stimulating factor-1 (CSF-1)" refers to a protein which exhibits the spectrum of activity understood in the art for CSF-1—i.e., when applied to the standard in vitro colony stimulating assay of Metcalf, D., *J Cell Physiol* (1970) 76:89, it results in the formation of primarily macrophage colonies. Native CSF-1 is a glycosylated dimer; dimerization may be necessary for activity. Contemplated within the scope of the invention and within the definition of CSF-1 are both the dimeric and monomeric forms. The monomeric form may be converted to the dimer by in vitro provision of intracellular conditions, and the monomer is per se useful as an antigen to produce anti-CSF-1 antibodies.

There appears to be some species specificity: Human CSF-1 is operative both on human and on murine bone marrow cells; murine CSF-1 does not show activity with human cells. Therefore, "human" CSF-1 should be positive in the specific murine radioreceptor assay of Das, S. K., et al, *Blood* (1981) 58:630, although there is not necessarily a complete correlation. The biological activity of the protein will generally also be inhibited by neutralizing antiserum to human urinary CSF-1 (Das, S. K., et al, supra). However, in certain special circumstances (such as, for example, where a particular antibody preparation recognizes a CSF-1 epitope not essential for biological function, and which epitope is not present in the particular CSF-1 mutein being tested) this criterion may not be met.

Certain other properties of CSF-1 have been recognized more recently, including the ability of this protein to stimulate the secretion of series E prostaglandins, interleukin-1, and interferon from mature macrophages (Moore, R., et al, *Science* (1984) 223:178). The mechanism for these latter activities is not at present understood, and for purposes of definition herein, the criterion for fulfillment of the definition resides in the ability to stimulate the formation of monocyte/macrophage colonies using bone marrow cells from the appropriate species as starting materials, under most circumstances (see above) the inhibition of this activity by neutralizing antiserum against purified human urinary CSF-1, and, where appropriate for species type, a positive response to the radioreceptor assay. (It is known that the proliferative effect of CSF-1 is restricted to cells of mononuclear phagocytic lineage (Stanley, E. R., *The Lymphokines* (1981), Stewart, W. E., II, et al, ed, Humana Press, Clifton, N.J.), pp. 102–132) and that receptors for CSF-1 are restricted to these cell lines (Byrne, P. V., et al, *Cell Biol* (1981) 91:848)).

As is the case for all proteins, the precise chemical structure depends on a number of factors. As ionizable amino and carboxyl groups are present in the molecule, a particular protein may be obtained as an acidic or basic salt, or in neutral form. All such preparations which retain their activity when placed in suitable environmental conditions are included in the definition. Further, the primary amino acid sequence may be augmented by derivatization using sugar moieties (glycosylation) or by other supplementary molecules such as lipids, phosphate, acetyl groups and the like, more commonly by conjugation with saccharides. The primary amino acid structure may also aggregate to form complexes, most frequently dimers. Indeed, native human urinary CSF-1 is isolated as a highly glycosylated dimer. Certain aspects of such augmentation are accomplished through post-translational processing systems of the producing host; other such modifications may be introduced in vitro. In any event, such modifications are included in the definition so long as the activity of the protein, as defined above, is not destroyed. It is expected, of course, that such modifications may quantitatively or qualitatively affect the activity, either by enhancing or diminishing the activity of the protein in the various assays.

Further, individual amino acid residues in the chain may be modified by oxidation, reduction, or other derivatization, and the protein may be cleaved to obtain fragments which retain activity. Such alterations which do not destroy activity do not remove the protein sequence from the definition.

Modifications to the primary structure itself by deletion, addition, or alteration of the amino acids incorporated into the sequence during translation can be made without destroying the activity of the protein. Such substitutions or other alterations result in proteins having an amino acid sequence which falls within the definition of proteins "having an amino acid sequence substantially equivalent to that of CSF-1". Indeed, human and murine derived CSF-1 proteins have non-identical but similar primary amino acid sequences which display a high homology.

For convenience, the mature protein amino acid sequence of the monomeric portion of a dimeric protein shown in FIG. 5, deduced from the cDNA clone illustrated herein, is designated mCSF-1 (mature CSF-1). FIG. 5 shows the presence of a 32 residue putative signal sequence, which is presumably cleaved upon secretion from mammalian cells; mCSF-1 is represented by amino acids 1–224 shown in that figure. Specifically included in the definition of human CSF-1 are muteins which monomers and dimers are mCSF-1 and related forms of mCSF-1, designated by their differences from mCSF-1. CSF-1 derived from other species may fit the definition of "human" CSF-1 by virtue of its display of the requisite pattern of activity as set forth above with regard to human substrate.

Also for convenience, the amino acid sequence of mCSF-1 will be used as a reference and other sequences which are substantially equivalent to this in terms of CSF-1 activity will be designated by referring to the sequence shown in FIG. 5. The substitution of a particular amino acid will be noted by reference to the amino acid residue which it replaces. Thus, for example, $ser_{90}CSF-1$ refers to the protein which has the sequence shown in FIG. 5 except that the amino acid at position 90 is serine rather than cysteine. Deletions are noted by a $\nabla$ followed by the number of amino acids deleted from the N-terminal sequence, or by the number of amino acids remaining when residues are deleted from the C-terminal sequence, when the number is followed by a minus sign. Thus, $\nabla_4 CSF-1$ refers to CSF-1 of FIGS. 5-1 and 5-2 wherein the first 4 amino acids from the N-terminus have been deleted; $\nabla_{130-}$ refers to CSF-1 wherein the last 94 amino acids following amino acid 130 have been deleted. Illustrated below are, for example, $asp_{59}CSF-1$, which contains an aspartic residue encoded by the gene (FIG. 4) at position 59 rather than the tyrosine residue encoded by the cDNA, and $\nabla_{158-}CSF-1$, which comprises only amino acids 1–158 of mCSF-1.

"Operably linked" refers to juxtaposition such that the normal function of the components can be performed. Thus, a coding sequence "operably linked" to control sequences refers to a configuration wherein the coding sequence can be expressed under the control of these sequences.

"Control sequences" refers to DNA sequences necessary for the expression of an operably linked coding sequence in a particular host organism. The control sequences which are suitable for procaryotes, for example, include a promoter, optionally an operator sequence, a ribosome binding site, and possibly, other as yet poorly understood, sequences. Eucaryotic cells are known to utilize promoters, polyadenylation signals, and enhancers.

"Expression system" refers to DNA sequences containing a desired coding sequence and control sequences in operable linkage, so that hosts transformed with these sequences are capable of producing the encoded proteins. In order to effect transformation, the expression system may be included on a vector; however, the relevant DNA may then also be integrated into the host chromosome.

As used herein "cell", "cell line", and "cell culture" are used interchangeably and all such designations include progeny. Thus "transformants" or "transformed cells" includes the primary subject cell and cultures derived therefrom without regard for the number of transfers. It is also understood that all progeny may not be precisely identical in DNA content, due to deliberate or inadvertent mutations. Mutant progeny which have the same functionality as screened for in the originally transformed cell, are included. Where distinct designations are intended, it will be clear from the context.

B. General Description

The CSF-1 proteins of the invention are capable both of stimulating monocyte-precursor/macrophage cell production from progenitor marrow cells, thus enhancing the effectiveness of the immune system, and of stimulating such functions of these differentiated cells as the secretion of lymphokines in the mature macrophages.

In one application, these proteins are useful as adjuncts to chemotherapy. It is well understood that chemotherapeutic treatment results in suppression of the immune system. Often, although successful in destroying the tumor cells against which they are directed, chemotherapeutic treatments result in the death of the subject due to this side effect of the chemotoxic agents on the cells of the immune system. Administration of CSF-1 to such patients, because of the ability of CSF-1 to mediate and enhance the growth and differentiation of bone marrow-derived precursors into macrophages and monocytes and to stimulate some of the functions of these mature cells, results in a restimulation of the immune system to prevent this side effect, and thus to prevent the propensity of the patient to succumb to secondary infection. Other patients who would be helped by such treatment include those being treated for leukemia through bone marrow transplants; they are often in an immunosuppressed state to prevent rejection. For these patients also, the immunosuppression could be reversed by administration of CSF-1.

In general, any subject suffering from immunosuppression whether due to chemotherapy, bone marrow transplantation, or other, accidental forms of immunosuppression such as disease (e.g., acquired immune deficiency syndrome) would benefit from the availability of CSF-1 for pharmacological use. In addition, subjects could be supplied enhanced amounts of previously differentiated macrophages to supplement those of the indigenous system, which macrophages are produced by in vitro culture of bone marrow or other suitable preparations treated with CSF-1. These preparations include those of the patient's own blood monocytes, which can be so cultured and returned for local or systemic therapy.

The ability of CSF-1 to stimulate production of lymphokines by macrophages and to enhance their ability to kill target cells also makes CSF-1 directly useful in treatment of neoplasms and infections.

CSF-1 -stimulates the production of interferons by murine-derived macrophage (Fleit, H. B., et al, *J Cell Physiol* (1981) 108:347), and human, partially purified, CSF-1 from MIAPaCa cells stimulates the poly(I):poly(C)-induced production of interferon and TNF from human monocytes as illustrated below. In addition, CSF-1 stimulates the production of myeloid CSF by human blood monocytes.

Also illustrated below is a demonstration of the ability of murine CSF-1 (from L-cell-conditioned medium) to stimulate normal C3H/HeN mouse peritoneal macrophages to kill murine sarcoma TU5 targets. This activity is most effective when the CSF-1 is used as pretreatment and during the effector phase. The ability of CSF-1 to do so is much greater than that exhibited by other colony stimulating factors, as shown in FIG. 6 hereinbelow. In addition, the ability of murine cells to attack viruses, is enhanced by CSF-1.

Murine CSF-1 is inconsistently reported to stimulate murine macrophage to be cytostatic to P815 tumor cells (Wing, E. J., et al, *J Clin Invest* (1982) 69:270) or not to kill other leukemia targets (Ralph, P, et al, *Cell Immunol* (1983) 76:10). Nogawa, R. T., et al, *Cell Immunol* (1980) 53:116, report that CSF-1 may stimulate macrophage to ingest and kill yeast.

Thus, in addition to overcoming immunosuppression per se, CSF-1 can be used to destroy the invading organisms or malignant cells indirectly by stimulation of macrophage secretions and activity.

The CSF-1 of the invention may be formulated in conventional ways standard in the art for the administration of protein substances. Administration by injection is preferred; formulations include solutions or suspensions, emulsions, or solid composition for reconstitution into injectables. Suitable excipients include, for example, Ringer's solution, Hank's solution, water, saline, glycerol, dextrose solutions, and the like. In addition, the CSF-1 of the invention may be preincubated with preparations of cells in order to stimulate appropriate responses, and either the entire preparation or the supernatant therefrom introduced into the subject. As shown hereinbelow, the materials produced in response to CSF-1 stimulation by various types of blood cells are effective against desired targets, and the properties of these blood cells themselves to attack invading viruses or neoplasms may be enhanced. The subject's own cells may be withdrawn and used in this way, or, for example, monocytes or lymphocytes from another compatible individual employed in the incubation.

Although the existence of a pattern of activity designated CSF-1 has been known for some time, the protein responsible has never been obtained in both sufficient purity and in sufficient amounts to permit sequence determination, nor in sufficient purity and quantity to provide a useful therapeutic function. Because neither completely pure practical amounts of the protein nor its encoding DNA have been available, it has not been possible to optimize modifications to structure by providing such alternatives as those set forth in ¶A above, nor has it been possible to utilize this protein in a therapeutic context.

The present invention remedies these defects. Through a variety of additional purification procedures, sufficient pure CSF-1 has been obtained from human urine to provide some amino acid sequence, thus permitting the construction of DNA oligomeric probes. The probes are useful in obtaining the coding sequence for the entire protein. One approach illustrated below, employs probes designed with respect to the human N-terminal sequence to probe the human genomic library to obtain the appropriate coding sequence portion. The human genomic cloned sequence can be expressed directly using its own control sequences, or in constructions appropriate to mammalian systems capable of processing introns. The genomic sequences are also used as probes for a human cDNA library obtained from a cell line which produces CSF-1 to obtain cDNA encoding this protein. The cDNA, when suitably prepared, can be expressed directly in COS or CV-1 cells and can be constructed into vectors suitable for expression in a wide range of hosts.

Thus these tools can provide the complete coding sequence for human CSF-1 from which expression vectors applicable to a variety of host systems can be constructed and the coding sequence expressed. The variety of hosts available along with expression vectors suitable for such hosts permits a choice among post-translational processing systems, and of environmental factors providing conformational regulation of the protein thus produced.

C. Suitable Hosts, Control Systems and Methods

In general terms, the production of a recombinant form of CSF-1 typically involves the following:

First a DNA encoding the mature (used here to include all muteins) protein, the preprotein, or a fusion of the CSF-1 protein to an additional sequence which does not destroy its activity or to additional sequence cleavable under controlled conditions (such as treatment with peptidase) to give an active protein, is obtained. If the sequence is uninterrupted by introns it is suitable for expression in any host. If there are introns, expression is obtainable in mammalian or other eucaryotic systems capable of processing them. This sequence should be in excisable and recoverable form. The excised or recovered coding sequence is then placed in operable linkage with suitable control sequences in a replicable expression vector. The vector is used to transform a suitable host and the transformed host cultured under favorable conditions to effect the production of the recombinant CSF-1. Optionally the CSF-1 is isolated from the medium or from the cells; recovery and purification of the protein may not be necessary in some instances, where some impurities may be tolerated. For example, for in vitro cultivation of cells from which a lymphokine factor will be isolated for administration to a subject, complete purity is not required. However, direct use in therapy by administration to a subject would, of course, require purification of the CSF-1 produced.

Each of the foregoing steps can be done in a variety of ways. For example, the desired coding sequences can be obtained by preparing suitable cDNA from cellular messenger and manipulating the cDNA to obtain the complete sequence. Alternatively, genomic fragments may be obtained and used directly in appropriate hosts. The constructions for expression vectors operable in a variety of hosts are made using appropriate replicons and control sequences, as set forth below. Suitable restriction sites can, if not normally available, be added to the ends of the coding sequence so as to provide an excisable gene to insert into these vectors.

The control sequences, expression vectors, and transformation methods are dependent on the type of host cell used to express the gene. Generally, procaryotic, yeast, or mammalian cells are presently useful as hosts. Since native CSF-1 is secreted as a glycosylated dimer, host systems which are capable of proper post-translational processing are preferred. Accordingly, although procaryotic hosts are in general the most efficient and convenient for the production of recombinant proteins, eucaryotic cells, and, in particular, mammalian cells are preferred for their processing capacity. Recombinant CSF-1 produced by bacteria would require in vitro dimerization. In addition, there is more assurance that the native signal sequence will be recognized by mammalian cell hosts making secretion possible, and purification therefore easier.

C.1. Control Sequences And Corresponding Hosts

Procaryotes most frequently are represented by various strains of *E. coli*. However, other microbial strains may also be used, such as bacilli, for example *Bacillus subtilis*, various species of Pseudomonas, or other bacterial strains. In such procaryotic systems, plasmid vectors which contain replication sites and control sequences derived from a species compatible with the host are used. For example, *E. coli* is typically transformed using derivatives of pBR322, a plasmid derived from an *E. coli* species by Bolivar, et al, *Gene* (1977) 2:95. pBR322 contains genes for ampicillin and tetracycline resistance, and thus provides additional markers which can be either retained or destroyed in constructing the desired vector. Commonly used procaryotic control sequences which are defined herein to include promoters for transcription initiation, optionally with an operator, along with ribosome binding site sequences, include such commonly used promoters as the beta-lactamase (penicillinase) and lactose (lac) promoter systems (Chang, et al, *Nature* (1977) 198:1056) and the tryptophan (trp) promoter system (Goeddel, et al *Nucleic Acids Res* (1980) 8:4057) and the lambda derived $P_L$ promoter and N-gene ribosome binding site (Shimatake, et al, *Nature* (1981) 292:128), which have been made useful as a portable control cassette, as set forth in U.S. Pat. No. 4,711,845, assigned to the same assignee. However, any available promoter system compatible with procaryotes can be used.

In addition to bacteria, eucaryotic microbes, such as yeast, may also be used as hosts. Laboratory strains of *Saccharomyces cerevisiae*, Baker's yeast, are most used although a number of other strains are commonly available. While vectors employing the 2 micron origin of replication are illustrated, Broach, J. R., *Meth Enz* (1983) 101:307, other plasmid vectors suitable for yeast expression are known (see, for example, Stinchcomb, et al, *Nature* (1979) 282:39, Tschempe, et al, *Gene* (1980) 10:157 and Clarke, L, et al, *Meth Enz* (1983) 101:300). Control sequences for yeast vectors include promoters for the synthesis of glycolytic enzymes (Hess, et al, *J Adv Enzyme Reg* (1968) 7:149; Holland, et al, *Biochemistry* (1978) 17:4900). Additional promoters known in the art include the promoter for 3-phosphoglycerate kinase (Hitzeman, et al, *J Biol Chem* (1980) 255:2073), and those for other glycolytic enzymes, such as glyceraldehyde-3-phosphate dehydrogenase, hexokinase, pyruvate decarboxylase, phosphofructokinase, glucose-6-phosphate isomerase, 3-phosphoglycerate mutase, pyruvate kinase, triosephosphate isomerase, phosphoglucose isomerase, and glucokinase. Other promoters, which have the additional advantage of transcription controlled by growth conditions, are the promoter regions for alcohol dehydrogenase 2, isocytochrome C, acid phosphatase, degradative enzymes associated with nitrogen metabolism, and enzymes responsible for maltose and galactose utilization (Holland, ibid). It is also believed terminator sequences are desirable at the 3' end of the coding sequences. Such terminators are found in the 3' untranslated region following the coding sequences in yeast-derived genes. Many of the vectors illustrated contain control sequences derived from the enolase gene containing plasmid peno46 (Holland, M. J., et al, *J Biol Chem* (1981) 256:1385) or the LEU2 gene obtained from YEp13 (Broach, J., et al, *Gene* (1978) 8:121), however, any vector containing a yeast compatible promoter, origin of replication and other control sequences is suitable.

It is also, of course, possible to express genes encoding polypeptides in eucaryotic host cell cultures derived from multicellular organisms. See, for example, *Tissue Culture*, Academic Press, Cruz and Patterson, editors (1973). Useful host cell lines include murine myelomas N51, VERO and HeLa cells, and Chinese hamster ovary (CHO) cells. Expression vectors for such cells ordinarily include promoters and control sequences compatible with mammalian cells such as, for example, the commonly used early and late promoters from Simian Virus 40 (SV 40). (Fiers, et al, *Nature* (1978) 273:113), or other vital promoters such as those derived from polyoma, Adenovirus 2, bovine papilloma virus, or avian sarcoma viruses, or immunoglobulin promoters and heat shock promoters. General aspects of mammalian cell host system transformations have been described by Axel; U.S. Pat. No. 4,399,216 issued 16 Aug. 1983. It now appears also that "enhancer" regions are important in optimizing expression; these are, generally, sequences found upstream of the promoter region. Origins of replication may be obtained, if needed, from viral sources. However, integration into the chromosome is a common mechanism for DNA replication in eucaryotes. Plant cells are also now available as hosts, and control sequences compatible with plant cells such as the nopaline synthase promoter and polyadenylation signal sequences (Depicker, A., et al, *J Mol Appl Gen* (1982) 1:561) are available.

C.2. Tran formations

Depending on the host cell used, transformation is done using standard techniques appropriate to such cells. The calcium treatment employing calcium chloride, as described by Cohen, S. N., *Proc Natl Acad Sci (USA)* (1972) 69:2110, is used for procaryotes or other cells which contain substantial cell wall barriers. Infection with *Agrobacterium tumefaciens* (Shaw, C. H., et al, *Gene* (1983) 23:315) is used for certain plant cells. For mammalian cells without such cell walls, the calcium phosphate precipitation method of Graham and van der Eb, *Virology* (1978) 52:546 is preferred. Transformations into yeast are carried out according to the method of Van Solingen, P., et al, *J Bact* (1977) 130:946 and Hsiao, C. L., et al, *Proc Natl Acad Sci (USA)* (1979) 76:3829.

C.3. Probing mRNA by Northern Blot; Probe of cDNA or Genomic Libraries

RNA is fractionated for Northern blot by agarose slab gel electrophoresis under fully denaturing conditions using formaldehyde (Maniatis, T., et al, *Molecular Cloning* (1982) Cold Spring Harbor Press, pp 202–203) or 10 mM methyl mercury ($CH_3HgOH$) (Bailey, J. M., et al, *Anal Biochem* (1976) 70:75–85; and Sehgal, P. B., et al, *Nature* (1980) 288:95–97) as the denaturant. For methyl mercury gels, 1.5% gels are prepared by melting agarose in running buffer (100 mM boric acid, 6 mM sodium borate, 10 mM sodium sulfate, 1 mM EDTA, pH 8.2 ), cooling to 60° C. and adding $\frac{1}{100}$ volume of 1M $CH_3HgOH$. The RNA is dissolved in 0.5× running buffer and denatured by incubation in 10 mM methyl mercury for 10 min at room temperature. Glycerol (20%) and bromophenol blue (0.05%) are added for loading the samples. Samples are electrophoresed for 500–600 volt-hr with recirculation of the buffer. After electrophoresis, the gel is washed for 40 min in 10 mM 2-mercaptoethanol to detoxify the methyl mercury, and Northern blots prepared by transferring the RNA from the gel to a membrane filter.

cDNA or genomic libraries are screened using the colony or plaque hybridization procedure. Bacterial colonies, or the plaques for phage are lifted onto duplicate nitrocellulose filter papers (S & S type BA-85). The plaques or colonies are lysed and DNA is fixed to the filter by sequential treatment for 5 min with 500 mM NaOH, 1.5M NaCl. The filters are washed twice for 5 min each time with 5× standard saline citrate (SSC) and are air dried and baked at 80° C. for 2 hr.

The gels for Northern blot or the duplicate filters for cDNA or genomic screening are prehybridized at 25°–42° C. for 6–8 hr with 10 ml per filter of DNA hybridization buffer without probe (0–50% formamide, 5–6 × SSC, pH 7.0, 5× Denhardt's solution (polyvinylpyrrolidine, plus Ficoll and bovine Serum albumin; 1×= 0.02% of each), 20–50 mM sodium phosphate buffer at pH 7.0, 0.2% SDS, 20 µg/ml poly U (when probing cDNA), and 50 µg/ml denatured salmon sperm DNA). The samples are then hybridized by incubation at the appropriate temperature for about 24–36 hours using the hybridization buffer containing kinased probe (for oligomers). Longer cDNA or genomic fragment probes were labeled by nick translation or by primer extension.

The conditions of both prehybridization and hybridization depend on the stringency desired, and vary, for example, with probe length. Typical conditions for relatively long (e.g., more than 30–50 nucleotide) probes employ a temperature of 42°–55° C. and hybridization buffer containing about 20%–50% formamide. For the lower stringencies needed for oligomeric probes of about 15 nucleotides, lower temperatures of about 25°–42° C., and lower formamide concentrations (0%–20%) are employed. For longer probes, the filters may be washed, for example, four times for 30 minutes, each time at 40°–55° C. with 2× SSC, 0.2% SDS and 50 mM sodium phosphate buffer at pH 7, then washed twice with 0.2× SSC and 0.2% SDS, air dried, and are autoradiographed at −70° C. for 2 to 3 days. Washing conditions are somewhat less harsh for shorter probes.

C.4. Vector Construction

Construction of suitable vectors containing the desired coding and control sequences employs standard ligation and restriction techniques which are well understood in the art. Isolated plasmids, DNA sequences, or synthesized oligonucleotides are cleaved, tailored, and religated in the form desired.

Site specific DNA cleavage is performed by treating with the suitable restriction enzyme (or enzymes) under conditions which are generally understood in the art, and the particulars of which are specified by the manufacturer of these commercially available restriction enzymes. See, e.g., New England Biolabs, Product Catalog. In general, about 1 µg of plasmid or DNA sequence is cleaved by one unit of enzyme in about 20 µl of buffer solution; in the examples herein, typically, an excess of restriction enzyme is used to insure complete digestion of the DNA substrate. Incubation times of about one hour to two hours at about 37° C. are workable, although variations can be tolerated. After each incubation, protein is removed by extraction with phenol/chloroform, and may be followed by ether extraction, and the nucleic acid recovered from aqueous fractions by precipitation with ethanol. If desired, size separation of the cleaved fragments may be performed by polyacnylamide gel or agarose gel electrophoresis using standard techniques. A general description of size separations is found in *Methods in Enzymology* (1980) 65:499–560.

Restriction cleaved fragments may be blunt ended by treating with the large fragment of *E. coli* DNA polymerase I (Klenow) in the presence of the four deoxynucleotide triphosphates (dNTPs) using incubation times of about 15 to 25 min at 20° to 25° C. in 50 mM Tris pH 7.6, 50 mM NaCl, 6 mM MgCl$_2$, 6 mM DTT and 5–10 µM dNTPs. The Klenow fragment fills in at 5' sticky ends but chews back protruding 3' single strands, even though the four dNTPs are present. If desired, selective repair can be performed by supplying only one of the, or selected, dNTPs within the limitations dictated by the nature of the sticky ends. After treatment with Klenow, the mixture is extracted with phenol/chloroform and ethanol precipitated. Treatment under appropriate conditions with S1 nuclease results in hydrolysis of any single-stranded portion.

Synthetic oligonucleotides may be prepared by the triester method of Matteucci, et al (*J Am Chem Soc* (1981) 103:3185–3191) or using automated synthesis methods.

Kinasing of single strands prior to annealing or for labeling is achieved using an excess, e.g., approximately 10 units of polynucleotide kinase to 1 nmole substrate in the presence of 50 mM Tris, pH 7.6, 10 mM MgCl$_2$, 5 mM dithiothreitol, 1–2 mM ATP. If kinasing is for labeling of probe, the ATP will contain high specific activity 32YP.

Ligations are performed in 15–30 µl volumes under the following standard conditions and temperatures: 20 mM Tris-Cl pH 7.5, 10 mM MgCl$_2$, 10 mM DTT, 33 µg/ml BSA, 10 mM-50 mM NaCl, and either 40 µM ATP, 0.01–0.02 (Weiss) units T4 DNA ligase at 0° C. (for "sticky end" ligation) or 1 mM ATP, 0.3–0.6 (Weiss) units T4 DNA ligase at 14° C. (for "blunt end" ligation). Intermolecular "sticky end" ligations are usually performed at 33–100 µg/ml total DNA concentrations (5–100 nM total end concentration). Intermolecular blunt end ligations (usually employing a 10–30 fold molar excess of linkers) are performed at 1 µM total ends concentration.

In vector construction employing "vector fragments", the vector fragment is commonly treated with bacterial alkaline phosphatase (BAP) in order to remove the 5' phosphate and prevent religation of the vector. BAP digestions are conducted at pH 8 in approximately 150 mM Tris, in the presence of Na$^+$ and Mg$^{+2}$ using about 1 unit of BAP per µg of vector at 60° for about one hour. In order to recover the nucleic acid fragments, the preparation is extracted with phenol/chloroform and ethanol precipitated. Alternatively, religation can be prevented in vectors which have been double digested by additional restriction enzyme digestion of the unwanted fragments.

C.5. Modification of DNA Sequences

For portions of vectors derived from cDNA or genomic DNA which require sequence modifications, site specific primer directed mutagenesis is used. This technique is now standard in the art, and is conducted using a primer synthetic oligonucleotide complementary to a single stranded phage DNA to be mutagenized except for limited mismatching, representing the desired mutation. Briefly, the synthetic oligonucleotide is used as a primer to direct synthesis of a strand complementary to the phage, and the resulting double-stranded DNA is transformed into a phage-supporting host bacterium. Cultures of the transformed bacteria are plated in top agar, permitting plaque formation from single cells which harbor the phage.

Theoretically, 50% of the new plaques will contain the phage having, as a single strand, the mutated form; 50% will have the original sequence. The plaques are hybridized with kinased synthetic primer at a temperature which permits hybridization of an exact match, but at which the mismatches with the original strand are sufficient to prevent hybridization. Plaques which hybridize with the probe are then picked, cultured, and the DNA recovered. Details of site specific mutation procedures are described below in specific examples.

C.6. Verification of Construction

In the constructions set forth below, correct ligations for plasmid construction are confirmed by first transforming *E. coli* strain MM294, or other suitable host, with the ligation mixture. Successful transformants are selected by ampicillin, tetracycline or other antibiotic resistance or using other markers depending on the mode of plasmid construction, as is understood in the art. Plasmids from the transformants are then prepared according to the method of Clewell, D. B., et al, *Proc Natl Acad Sci (USA)* (1969) 62:1159, optionally following chloramphenicol amplification (Clewell, D. B., *J Bacteriol* (1972) 110:667). The isolated DNA is analyzed by restriction and/or sequenced by the dideoxy method of Sanger, F., et al, *Proc Natl Acad Sci (USA)* (1977) 74:5463 as further described by Messing, et al, *Nucleic Acids Res* (1981) 9:309, or by the method of Maxam, et al, *Methods in Enzymology* (1980) 65:499.

C.7. Hosts Exemplified

Host strains used in cloning and expression herein are as follows:

For cloning and sequencing, and for expression of construction under control of most bacterial promoters, *E. coli* strain MM294 obtained from *E. coli* Genetic Stock Center GCSC #6135, was used as the host. For expression under control of the $P_L N_{RBS}$ promoter, *E. coli* strain K12 MC1000 lambda lysogen, $N_7 N_{53} cI857$ SusP80, ATCC 39531 is used.

For M13 phage recombinants, *E. coli* strains susceptible to phage infection, such as *E. coli* K12 strain DG98, are employed. The DG98 strain has been deposited with ATCC 13 Jul. 1984 and has accession number 39768.

Mammalian expression has been accomplished in COS-7 and CV-1 cells.

D. Preferred Embodiments

The recombinant CSF-1 of the invention can be considered a set of muteins which have similar but not necessarily identical primary amino acid sequences, all of which exhibit, or are specifically cleavable to a mutein which exhibits, the activity pattern characteristic of CSF-1—i.e. they are capable of stimulating bone marrow cells to differentiate into monocytes, preponderantly, and, within the limitations set forth in the Definitions section above, are immunoreactive with antibodies raised against native CSF-1 and with the receptors associated with CSF-1 activity. Certain embodiments of these muteins are, however, preferred.

The primary sequence shown in FIGS. 5-1 and 5-2 for mCSF-1 has the required activity, and it is, of course, among the preferred embodiments. Also preferred are muteins wherein certain portions of the sequence have been altered by either deletion of, or conservative substitution of, one or more amino acids in mCSF-1. By a "conservative" amino acid substitution is meant one which does not change the activity characteristics of the protein, and in general is characterized by chemical similarity of the side chains of the two residues interchanged. For example, acidic residues are conservatively replaced by other acidic residues, basic by basic, hydrophobic by hydrophobic, bulky by bulky, and so forth. The degree of similarity required depends, of course, on the criticality of the amino acid for which substitution is made, and its nature. Thus, in general, preferred substitutions for cysteine residues are serine and alanine; for aspartic acid residues, glutamic acid; for lysine or arginine residues, histidine; for leucine residues, isoleucine, or valine; for tryptophan residues, phenylalanine or tyrosine; and so forth.

Regions of the CSF-1 protein which are most tolerant of alteration include those regions of known low homology between human and mouse species (residues 15–20 and 75–84); regions which confer susceptibility to proteolytic cleavage (residues 51 and 52 and residues 191–193); cysteine residues not participating in disulfide linkages, or which are not absolutely essential for activity (residues 159–224). It also appears residues 151–224 are not essential.

Therefore, particularly preferred are those CSF-1 muteins characterized by the deletion or conservative substitution of one or more amino acids and/or one or more sequences of amino acids between positions 159 and 224 inclusive of mCSF-1 or positions 151–224 inclusive. In particular, $\nabla_{158}$-CSF-1 has CSF activity comparable to that of the native protein, even if a limited number of additional amino acid residues not related to CSF-1 are included at the truncated C-terminus; $\nabla_{150}$-CSF-1 has similar activity. Indeed, the native protein is reported to have a molecular weight of 14–15 kd (as opposed to the 26 kd predicted from the cDNA sequence) and the hydrophobicity deduced from the recombinant (predicted) amino acid sequence corresponds to a transmembrane region normally susceptible to cleavage. It may, therefore, be that the truncated version corresponds in a rough way to the CSF-1 as isolated.

Also preferred are muteins characterized by the deletion or conservative substitution of one or more of the amino acids at positions 51 and 52 and/or positions 191, 192 and 193 of mCSF-1. Especially preferred is $gln_{52}$CSF-1; a corresponding proline substitution is not conservative, and does not yield an active CSF. Since they represent regions of apparently low homology, another preferred set of embodiments is that characterized by the deletion or conservative substitution of one or more of the amino acids at positions 15–20 and/or positions 75–84 of mCSF-1. Also preferred are those muteins characterized by the deletion or conservative substitution of/the cysteine residue at any position not essential for disulfide bond formation. Also preferred are those muteins characterized by the deletion or substitution of the tyrosine residue at position 59 of mCSF-1; particularly substitution by an aspartic acid residue.

E. Cloning and Expression of Human CSF-1

The following illustrates the methods used in obtaining the coding sequence for human CSF-1, for disposing this sequence in expression vectors, and for obtaining expression of the desired protein.

E.1. Purification of Native Human CSF-1 and Probe Design

Human urinary CSF-1 was partially purified by standard methods as described by Das, S. K., et al, *Blood* (1981) 58:630, followed by an affinity purification step using a rat monoclonal antibody to murine CSF-1, designated YYG106, attached to a Sepharose B column (Stanley, E. R., *Methods Enzymol* (1985) 116:564). The final step in purification was reverse phase HPLC in a 0.1% TFA/30% acetonitrile—0.1% TFA/60% acetonitrile buffer system.

For MIAPaCa CSF-1, which was produced serum-free by induction with phorbol myristic acetate, the cell supernatant was subjected to calcium phosphate gel chromatography (according to Das (supra)), followed by affinity chromatography using lentil lectin (in place of the ConA affinity step of Das), and then to the immunoaffinity step employing the YYG106 monoclonal antibody conjugated to Sepharose B and to the reverse phase HPLC, both as above described.

The urinary and MIAPaCa proteins, having been purified to homogeneity, were subjected to amino acid sequencing using Edman degradation on an automated sequencer. Sufficient N-terminal sequence of human CSF was determined to permit construction of probes shown in FIG. 3.

E.2. Preparation of the Human Genomic Sequence

A human genomic sequence encoding CSF-1 was obtained from the Maniatis human genomic library in λ phage Charon 4 using probes designed to encode the N-terminal sequence of human protein. The library was constructed using partial HaeIII/AluI digestion of the human genome, ligation to EcoRI linkers, and insertion of the fragments into EcoRI digested Charon 4 phage. A Charon 4A phage containing the CSF-1 sequence as judged by hybridization to probe as described below, and designated pHCSF-1, was deposited with the American Type Culture Collection (ATCC) on 2 Apr. 1985 and has accession no. 40177. Upon later study of this phage, it was found that rearrangements and/or deletions had occurred and the correct sequences were not maintained. Therefore, an alternative colony obtained from the genomic library in identical fashion, and propagated to confirm stability through replication, was designated pHCSF-1a and was deposited with ATCC on 21 May 1985, and given accession number 40185. pHCSF-1a contained an 18 kb insert and was capable of generating restriction enzyme digests which also hybridized to probe, and was used for sequence determination and additional probe construction as outlined below.

If the CSF-1 encoding sequence is present in its entirety its presence can be demonstrated by expression in COS-7 cells, as described by Gluzman, Y., *Cell* (1981) 23:175. The test fragment is cloned into a plasmid derived from pBR322 which has been modified to contain the SV40 origin of replication (pGRI Ringold, G., *J Mol Appl Genet* (1982) 1:165–175). The resulting high copy number vectors are transformed into COS-7 cells and expression of the CSF-1 gene assayed after 24, 48, and 72 hours by the radioreceptor assay method described by Das (supra). Expression is under control of the native CSF-1 control sequences. The HindIII digests of the approximately 18 kb insert of pHCSF-1a tested in this manner failed to express, thus indicating that HindIII digests into the gene. This was confirmed by subsequent mapping.

However, for initial sequencing, a 3.9 kb HindIII fragment was obtained from the pHCSF-1a phage and cloned into M13 cloning vectors.

The HindIII fragment has been partially sequenced, and the results are shown in FIG. 4, along with a deduced peptide sequence. It contains the correct codons for the portion of the human CSF-1 protein for which the amino acid sequence had been determined, as set forth in FIG. 1. The presence of an intron of approximately 1400 bp was deduced from the available amino acid sequence. In addition, based on the genomic sequence encoding amino acids 24–34 (see overlined portion of FIGS. 4 and 5), a 32-mer probe for the cDNA library was constructed and employed as described below.

In more detail, to obtain the genomic clone, pHCSF-1a, the Maniatis library was probed using two mixtures of oligomers shown in FIG. 3. EK14 and EK15 were selected, although the other oligomers shown are useful as well. A "full length" probe for the N-terminal sequence, EK14, was used as a mixture of sixteen 35-mers. A shorter oligomer, EK15, was employed as a mixture of sixty-four 18-mers. Phage hybridizing to both kinased probes were picked and cultured by infection of *E. coli* DG98 or other competent strain.

Specific conditions for probing with EK14 and EK15 are as follows: for EK14, the buffer contained 15% formamide, 6× SSC, pH 7.0, 5× Denhardt's, 20 mM sodium phosphate, 0.2.% SDS and 50 µg/ml denatured salmon sperm DNA. Prehybridization and hybridization were conducted at 42° C. and the filters were-washed in 2× SSC at 52° C. For EK15, similar conditions were used for hybridization and prehybridization except for the formamide concentration, which was 0%; washing was at a slightly lower temperature, 42° C.

The approximately 18 kb DNA insert isolated from the positively hybridizing phage pHCSF-1a was treated with HindIII and the fragments were subjected to electrophoresis on agarose gel according to the method of Southern. The gels were replicated onto nitrocellulose filters and the filters were probed again with EK14 and EK15. Both probes hybridized to a 3.9 kb fragment.

The positive fragment was excised from the gel, eluted, and subcloned into HindIII-treated M13mp19 for dideoxy sequencing. A partial sequence is shown in FIG. 4. The underlining corresponds precisely to the previously determined N-terminal sequence of human CSF-1; the residues with dot subscripts are homologous to the murine sequence.

In FIG. 4, the 1.4 kb intron region between the codons for amino acids 22 and 23, as deduced from the human sequence determined from the purified protein, is shown untranslated. The sequence upstream of the N-terminal residues contains the putative leader; the translation of the portion of this leader immediately adjacent to the mature protein, which was tentatively verified by the preliminary results of sequencing of the cDNA clone (see below) is shown. The upstream portions are, however, not shown translated; these portions are confirmed by comparison to the cDNA to comprise an intron.

Further sequencing to obtain about 13 kb of the entire 18 kb gene shows that the gene contains 9 exons separated by 8 introns. The regions of the mature protein cDNA correspond exactly to the genomic exon codons except for codon 59, as fur%her described below.

An additional M13 subclone was obtained by digestion of the HindIII 3.9 kb fragment with PstI to generate a 1 kb PstI/PstI fragment which includes the known N-terminal sequence and about 1 kb of additional upstream sequence.

E.3. cDNA Encoding Human CSF-1 pcCSF-17

The human derived pancreatic carcinoma cell line MIA-PaCa-2 was used as a source of mRNA to validate probes and for the formation of a cDNA library containing an intronless form of the human CSF-1 coding sequence. The MIAPaCa cell line produces CSF-1 at a level approximately 10 fold below that of the murine L-929 cells.

Negative control mRNA was prepared from MIAPaCa cells maintained in serum-free medium, i.e. under conditions wherein they do not produce CSF-1. Cells producing CSF-1 were obtained by reinducing CSF-1 production after removal of the serum.

Cells were grown to confluence in roller bottles using Dulbecco's Modified Eagles' Medium (DMEM) containing 10% fetal calf serum, and produce CSF-1 at 2000–6000 units/ml. The cell cultures were washed, and reincubated serum-free to suppress CSF-1 formation. For negative controls, no detectable CSF-1 was produced after a day or two. Reinduced cells were obtained by addition of phorbol myristic acetate (100 ng/ml) to obtain production after several days of 1000–2000 units/ml.

The mRNA was isolated by lysis of the cell in isotonic buffer with 0.5% NP-40 in the presence of ribonucleoside vanadyl complex (Berger, S. L., et al, *Biochemistry* (1979) 18:5143) followed by phenol chloroform extraction, ethanol precipitation, and oligo dT chromatography, and an enriched mRNA preparation obtained. In more detail, cells are washed twice in PBS (phosphate buffered saline) and are resuspended in IHB (140 mM NaCl, 10 mM Tris, 1.5 mM $MgCl_2$, pH 8) containing 10 mM vanadyl adenosine complex (Berger, S. L., et al, supra).

A non-ionic detergent of the ethylene oxide polymer type (NP-40) is added to 0.5% to lyse the cellular, but not nuclear membranes. Nuclei are removed by centrifugation at 1,000×g for 10 min. The post-nuclear supernatant is added to two volumes of TE (10 mM Tris, 1 mM ethylenediaminetetraacetic acid (EDTA), pH 7.5) saturated phenol chloroform (1:1) and adjusted to 0.5% sodium dodecyl sulfate (SDS) and 10 mM EDTA. The supernatant is re-extracted 4 times and phase separated by centrifugation at 2,000×g for 10 min. The RNA is precipitated by adjusting the sample to 0.25M NaCl, adding 2 volumes of 100% ethanol and storing at −20° C. The RNA is pelleted at 5,000×g for 30 min, is washed with 70% and 100% ethanol, and is then dried. Polyadenylated (poly $A^+$) messenger RNA (mRNA) is obtained from the total cytoplasmic RNA by chromatography on oligo dT cellulose (Aviv, J., et al, *Proc Natl Acad Sci* (1972) 69:1408–1412). The RNA is dissolved in ETS (10 mM Tris, 1 mM EDNA, 0.5% SDS, pH 7.5) at a concentration of 2 mg/ml. This solution is heated to 65° C. for 5 min, then quickly chilled to 4° C. After bringing the RNA solution to room temperature, it is adjusted to 0.4M NaCl and is slowly passed through an oligo dT cellulose column previously equilibrated with binding buffer (500 mM NaCl, 10 mM Tris, 1 mM EDTA, pH 7.5 0.05% SDS). The flow-through is passed over the column twice more. The column is then washed with 10 volumes of binding buffer. Poly $A^+$ mRNA is eluted with aliquots of ETS, extracted once with TE-saturated phenol chloroform and is precipitated by the addition of NaCl to 0.2M and 2 volumes of 100% ethanol. The RNA is reprecipitated twice, is washed once in 70% and then in 100% ethanol prior to drying.

Figure 7:
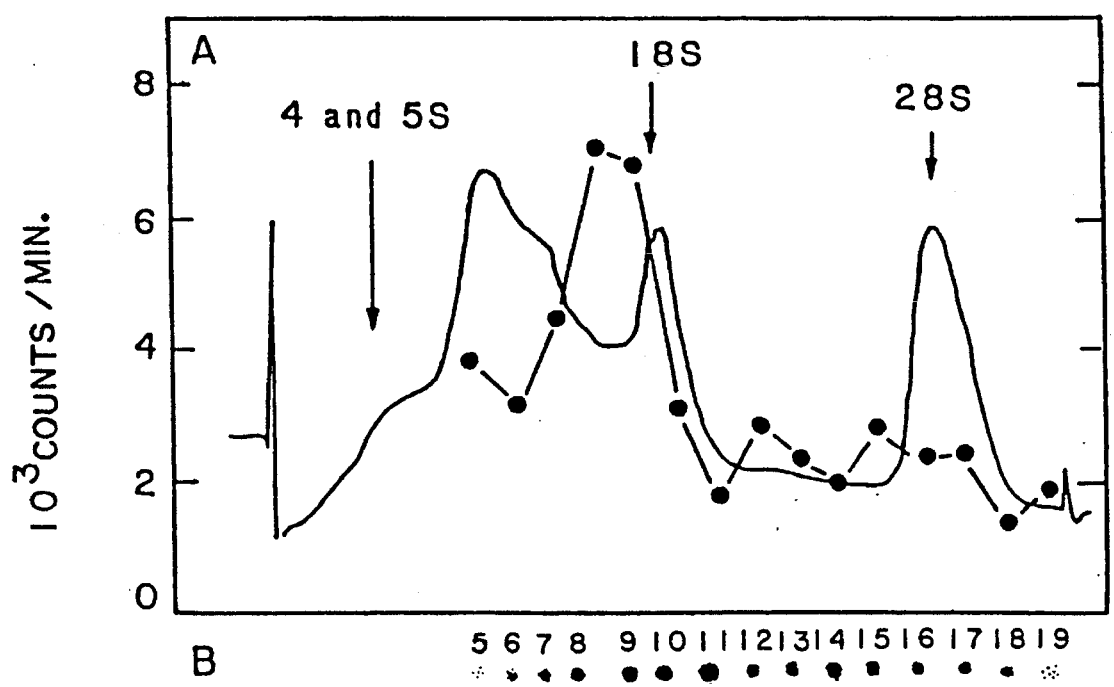
FIG. 7 shows the results of sucrose gradient fractionation of MIAPaCa mRNA.

Total mRNA was subjected to 5–20% by weight sucrose gradient centrifugation in 10 mM Tris HCl, pH 7.4, 1 mM EDTA, and 0.5% SDS using a Beckman SW40 rotor at 20° C. and 27,000 rpm for 17 hr. The mRNA fractions were then recovered from the gradient by ethanol precipitation, and injected into Xenopus oocytes in the standard translation assay. The oocyte products of the RNA fractions were assayed in the bone marrow proliferation assay (as described by Moore, R. N., et al, *J Immunol* (1983) 131:2374, and of Prystowsky, M. B., et al, *Am J Pathol* (1984) 114:149) and the fractions themselves were assayed by dot blot hybridization to a 32-mer probe corresponding to the DNA in the second exon of the genomic sequence (exon II probe). (The overlining in FIGS. 4 and 5-1 shows the exon II probe.) These results are summarized in FIG. 7.

The broken line in FIG. 7A shows the response in the bone marrow proliferation assay of the supernatants from the Xenopus oocytes; FIG. 7B shows the dot-blot results. The most strongly hybridizing fraction, 11, corresponds to a size slightly larger than the 18S markers, while the most active fractions 8 and 9 correspond to 14–16S. Fractions 8, 9 and 11 were used to form an enriched cDNA library as described below.

(The mRNA was also fractionated on a denaturing formaldehyde gel, transferred to nitrocellulose, and probed with exon II probe. Several distinct species ranging in size from 1.5 kb to 4.5 kb were found, even under stringent hybridization conditions. To eliminate the possibility of multiple genes encoding CSF-1, digests of genomic DNA with various restriction enzymes were subjected to Southern blot and probed using pCSF-17 DNA. The restriction pattern was consistent with the presence of only one gene encoding CSF-1.)

The enriched mRNA pool was prepared by combining the mRNA from the gradient fractions (8 and 9) having the highest bone marrow proliferative activity, although their ability to hybridize to probe is relatively low (14S–16S) with the fraction (II) hybridizing most intensely to probe (slightly larger than 18S). Higher molecular weight fractions which also hybridized to exon II probe were not included because corresponding mRNA from uninduced MIAPaCa cells also hybridized to exonII probe.

cDNA libraries were prepared from total or enriched human mRNA in two ways. One method uses λgt10 phage vectors and is described by Huynh, T. V., et al, in *DNA Cloning Techniques: A Practical Approach* IRL Press, Oxford 1984, D. Glover, Ed.

A preferred method uses oligo dT priming of the poly A tails and AMV reverse transcriptase employing the method of Okayama, H., et al. *Mol Cell Biol* (1983) 3:280–289, incorporated herein by reference. This method results in a higher proportion of full length clones than does poly dG tailing and effectively uses as host vector portions of two vectors therein described, and readily obtainable from the authors, pcDV1 and pL1. The resulting vectors contain the insert between vector fragments containing proximal BamHI and XhoI restriction sites; the vector contains the pBR322 origin of replication, and Amp resistance gene and SV40 control elements which result in the ability of the vector to effect expression of the inserted sequences in COS-7 cells.

A 300,000 clone library obtained from above enriched MIAPaCa mRNA by the Okayama and Berg method was then probed under conditions of high stringency, using the exon II probe. Ten colonies hybridizing to the probe were picked and colony purified. These clones were assayed for the presence of CSF-1 encoding sequences by transient expression in COS-7 cells. The cloning vector, which contains the SV40 promoter, was used per se in the transformation of COS-7 cells.

Plasmid DNA was purified from the 10 positive clones using a CsCl gradient, and the COS-7 cells transfected using a modification (Wang, A. M., et al, *Science* (1985) 228:149) of the calcium phosphate coprecipitation technique. After incubation for three days, CSF-1 production was assayed by subjecting the culture supernatants to the radioreceptor assay performed substantially as disclosed by Das, S. K., et al, *Blood* (1981) 58:630, and to a colony stimulation (bone marrow proliferation) assay performed substantially as disclosed by Prystowsky, M. B., et al, *Am J Pathol* (1984) 114: 149. Nine of the ten clones picked failed to show transient CSF-1 production in COS-7 cells. One clone, which did show expression, was cultured, the plasmid DNA isolated, and the insert was sequenced. The DNA sequence, along with the deduced amino acid sequence, are shown in FIG. 5. The full length cDNA is 1.64 kb and encodes a mature CSF-1 protein of 224 amino acids. The clone was designated CSF-17 with Cetus depository number CMCC 2347 and was deposited with the American Type Culture Collection on 14 Jun. 1985, as accession no. 53149. The plasmid bearing the CSF-1 encoding DNA was designated pcCSF-17.

Mutein-Encoding Sequences

Modifications were made of the pcCSF-17 inserts to provide corresponding plasmids encoding muteins of the mCSF-1 protein. For site-specific mutagenesis, pcCSF-17 and M13mp18 were digested with the same restriction enzyme excising the appropriate region of the CSF-1 coding sequence, and the excised sequence ligated into the M13 vector. Second strand synthesis and recovery of the desired mutated DNA used the following oligonucleotide primers:

for $pro_{52}$CSF-1, 5'-TACCTTAAACCGGCATTTCTC-3', which creates a new HpaII site at codons 52–53;

for $gln_{52}$CSF-1, 5'-TACCTTAAACAGGCCTTTCTC-3', which creates a new StuI site at codons 52–53;

for $asp_{59}$CSF-1, 5'-GGTACAAGATATCATGGAG-3', which creates a new EcoRV site at codons 59–60.

After second strand extension using Klenow, the phage were transformed into *E coli* DG98 and the resulting plaques screened with kinased labeled probe. After plaque purification, the desired mutated inserts were returned to replace the unmutated inserts in pcCSF-1, yielding pCSF-pro52, pCSF-gln52, and pCSF-asp59, respectively.

Plasmids containing three deletion mutants which encode $\nabla_{158}$-CSF-1 were also prepared: pCSF-Bam, pCSF-Bam-Bcl, and pCSF-BamTGA. For pCSF-Bam, pcCSF-17 was digested with BamHI, and the upstream BamHI/BamHI fragment of the coding region was isolated and religated to the vector fragment. The ligation mixture was transformed into *E coli* MM294 and plasmids with the correct orientation isolated. The resulting pCSF-Bam encodes 158 amino acids of the CSF-1 protein fused to six residues derived from the vector at the C-terminus: arg-his-asp-lys-ile-his.

For pCSF-BamBcl, which contains the entire CSF-1 encoding sequence, except that the serine at position 159 is mutated to a stop codon, the coding sequence was excised from pcCSF-17 and ligated into M13 for site-specific mutagenesis using the primer: 5'-GAGGGATCCTGAT-CACCGCAGCTCC-3'. This results in a new BclI site at codons 159–160. The mutated DNA was excised with BstXI/EcoRI and ligated into the BstXI/EcoRI digested pcCSF-17, the ligation mixture was transformed into *E coli* DG105, a dam⁻ host, and the plasmid DNA isolated.

For pCSF-BamTGA, in which the codons downstream of the 159-stop are deleted. pCSF-BamBcl was digested with XhoI and BclI, and the insert ligated into XhoI/BamHI digested pcCSF-17.

In addition, pCSF-Gly150, which contains a TGA stop codon instead of histidine at position 151, was prepared from the pcCSF-17 insert by site-specific mutagenesis using the appropriate primer, as described above.

E.4. Transient Expression of CSF-1

Expression of pcCSF-17

The expression of plasmid DNA from CSF-17 (pcCSF-17) in COS-7 cells was confirmed and guantitated using the bone marrow proliferation assay, the colony stimulation assay and the radioreceptor assay. It will be recalled that the specificity of the bone marrow proliferation assay for CSF-1 resides only in the ability of CSF-1 antiserum to diminish activity; that for the colony stimulation assay, in the nature of the colonies obtained. Both assays showed CSF-1 production to be of the order of several thousand units per ml.

Bone Marrow Proliferation

For the bone marrow stimulation assay, which measures biological activity of the protein, bone marrow cells from Balb/C mice were treated with serial dilutions of the 72 hour supernatants and proliferation of the cells was measured by uptake of labeled thymidine, essentially as described by Moore, R. N., et al. *J Immunol* (1983) 131:2374; Prystowsky, M. B., et al. *Am J Pathol* (1984) 114:149. The medium from induced MIAPaCa cells was used as control. Specificity for CSF-1 was confirmed by the ability of rabbit antisera raised against human urinary CSF-1 to suppress thymidine uptake. The results for COS-7 cell supernatants transfected with pcCSF-17 (CSF-17 supernatant) at a 1:16 dilution are shown in Table 1.

TABLE 1

|  | $^3$H-thymidine incorporation (cpm) | | |
| --- | --- | --- | --- |
|  | no add'ns | normal serum | antihuman CSF-1 serum |
| medium | 861 | 786 | 2682 |
| MIAPaCa supernate | 12255 | 16498 | 3302 |
| CSF-17 supernate | 16685 | 21996 | 2324 |

(The antihuman CSF-1 serum was prepared as described by Das, et al, supra.)

The MIAPaCa supernatant (at the 1:16 dilution used above) contained 125 U/ml CSF activity corresponding to 2000 U/ml in the undiluted supernatant, where 1 unit of colony stimulating activity is defined as the amount of CSF needed to produce one colony from $10^5$ bone marrow cells/ml in the assay of Stanley, E. R., et al, *J Lab Clin Med* (1972) 79:657.

These data show that the bone marrow stimulating activity is associated with CSF-1, since thymidine uptake is inhibited by anti-CSF-1 serum. Regression of results in this bone marrow proliferation assay obtained at four dilutions ranging from 1:8 to 1:64 gave an estimated activity for CSF-1 in CSF-17 supernatants of 2358 U/ml, which was diminished to 424 U/ml in the presence of antiserum, but showed an apparent increase to 3693 U/ml in the presence of non-immune serum. This was comparable to the levels shown in the radioreceptor assay below.

Colony Stimulation

Direct assay of the CSF-17 supernatants for colony stimulation (Stanley, E. R., et al, *J Lab Clin Med* (supra)) showed 4287 U/ml, which was substantially unaffected by the presence of non-immune serum but reduced to 0 U/ml in the presence of rabbit antihuman CSF-1. This compares to 2562 U/ml in the MIAPaCa supernatants. Eighty-five percent of the pcCSF-17 transformed COS-7 supernatant induced colonies had mononuclear morphology; MIAPaCa supernatant induced colonies showed a 94% macrophage-6% granulocyte ratio.

Radioreceptor Assay

The radioreceptor assay measures competition between $^{125}$I-labeled CSF-1 and the test compound for specific receptors on J774.2 mouse macrophage cells. MIAPaCa supernatant, assayed for colony stimulating activity as above, was used as a standard (2000 U/ml). The CBF-1 concentration of the pcCSF-17 transformed COS-7 supernatant was found to be 2470 U/ml based on a 1:10 dilution and 3239 U/ml based on a 1:5 dilution..

Thus, comparable values for CSF-1 concentration in the media of COS-7 cells transformed with pcCSF-17 were found in all assays.

Expression of Muteins

In a similar manner to that described above for pcCSF-17, the mutein-encoding plasmids were transfected into COS-A2 cells and transient expression of CBF-1 activity assayed by the bone marrow proliferation assay and by radioimmunoassay using anti-CSF antibodies. The expression product of pCSF-pro52 was inactive, indicating that, as expected, substitution by proline is not conservative. All other muteins showed activity in both assays as shown by the results below:

Expression of CSF-1 Constructs in COS Cells

| CSF-1 Plasmid | Radio-immunoassay (units/ml) | Bone Marrow Assay (units/ml) | |
|---|---|---|---|
| | | Proliferation (units/ml) | Colony |
| pcCSF-17 | 3130 | 2798 | 11,100 |
| | 3080 | 3487 | 9750 |
| | 3540 | 3334 | 11,500 |
| pCSF-pro52 | 54.8 | <25 | <100 |
| | 51.9 | <25 | <100 |
| | 45.3 | <25 | <100 |
| pCSF-gln52 | 1890 | 2969 | 6200 |
| | 2250 | 2308 | 5500 |
| | 1910 | 2229 | 4400 |
| pCSF-asp59 | 3210 | 3381 | 9000 |
| | 4680 | 3417 | 6800 |
| | 3470 | 2812 | 10,600 |
| pCSF-Bam | 9600 | 8048 | 22,600 |
| | 8750 | 8441 | 21,900 |
| | 8400 | 10,995 | 21,700 |
| pCSF-BamBcl | 8800 | | 26,000 |
| | 10,700 | | 21,600 |
| | 15,450 | | 24,200 |
| pCSF-BamTGA | 8450 | | 22,600 |
| | 7550 | | 23,200 |
| | 9700 | | 20,000 |
| pCSF-Gly150 | 26,850 | | 55,710 |

E.5. Stable Expression of CSF-1

The COS-7 system provides recombinant CSF-1 by permitting replication of and expression from the vector sequences. It is a transient expression system.

The human CSF-1 sequence can also be stably expressed in procaryotic or eucaryotic systems. In general, procaryotic hosts offer ease of production, while eucaryotes permit the use of the native signal sequence and carry out desired post-translational processing. This may be especially important in the case of CSF-1 since the native protein is a dimer. Bacteria produce CSF-1 as a monomer, which would then be subjected to dimerizing conditions after extraction.

Procaryotic Expression

For procaryotic expression, the cDNA clone, or the genomic sequence with introns excised by, for example, site-specific mutagenesis, is altered to place an ATG start codon immediately upstream of the glutamic acid at the N-terminus, and a HindIII site immediately upstream of the ATG in order to provide a convenient site for insertion into the standard host expression vectors below. This can be done directly using insertion site-specific mutagenesis with a synthetic oligomer containing a new sequence complementary to the desired AAGCTTATG, flanked by nucleotide sequences complementary to the native leader and N-terminal coding sequences.

For cDNA obtained using the method of Okayama and Berg, the DNA fragment containing the entire coding sequence is excised from pcCSF-17 or the corresponding mutein vector by digestion with XhoI (at sites retained from the host cloning vector), isolated by agarose gel electrophoresis, and recovered by electroelution. To carry out the mutagenesis, the host bacteriophage M13mp18 DNA is also treated with SalI and ligated with the purified fragment under standard conditions and transfected into frozen competent $E.\ coli$ K12 strain DG98. The cells are plated on media containing $5 \times 10^{-4}$M isopropyl thiogalactoside (IPTG) obtained from Sigma Chem. (St. Louis, Mo.) and 40 µg/ml X-gal. Non-complementing white plaques are picked into fresh media. Mini-cultures are screened for recombinant single strand phage DNA of the expected size, and the structure of the desired recombinant phage is confirmed using restriction analysis.

A 34-mer complementary to the N-terminal and leader encoding portions of the CSF-1 sequence, but containing the complement to the desired AAGCTTATG sequence is synthesized and purified according to the procedures set forth in ¶C.4. A portion of this 34-mer preparation is radiolabeled according to a modification of the technique of Maxam and Gilbert (Maxam, A., et al, *Methods in Enzymology* (1980) 68:521, Academic Press) as set forth in C.4 above.

To perform the mutagenesis the above prepared recombinant bacteriophage is prepared in $E.\ coli$ K12 strain DG98 and the single strand phage DNA purified. One pmole of single strand phage DNA and 10 pmoles of the above synthetic nucleotide primer (not kinased) are annealed by heating for 1 min at 67° C., and then 30 min at 37° C. in 15 µl 20 mM Tris-Cl, pH 8, 20 mM MgCl$_2$, 100 mM NaCl, 20 mM 2-mercaptoethanol. The annealed DNA is incubated with DNA polymerase I (Klenow) and 500 µM dNTPs for 30 min. 0° C. and then brought to 37° C. Aliquots (0.05 or 0.25 pmole) are removed after 5 min, 20 min, and 45 min, transformed into $E.\ coli$ K12 strain DG98 and plated.

After growth, the plates are chilled at 4° C. and plaques lifted with PalI membranes obtained from Biodyne or S&S filters (1–2 min in the first filter, more than 10 min for the second filter). The filters are denatured in 2.5M NaCl, 0.5M NaOH (5 min). The denaturing medium is neutralized with 3M sodium acetate to pH 5.5, or with 1M Tris-Cl, pH 7.5 containing 1M NaCl, the filters baked at 80° C. in vacuo for 1 hr, and then prehybridized at high stringency. The filters are then probed with the kinased synthetic 34-mer prepared above at high stringency, washed, and autoradiographed overnight at -70° C.

The RF form of the desired mutated phage is treated with EcoRI, blunted with Klenow, and then digested with HindIII to excise the gene as a HindIII/blunt fragment. (In a strictly analogous manner, the CSF-1 encoding sequence from pMCSF may be obtained and modified.)

This fragment containing the human (or murine) CSF-1 encoding sequence is then ligated with HindIII/BamHI (blunt) digested pPLOP or pTRP3 (see below) to place the coding sequence containing the ATG start codon immediately downstream from the $P_L$ or trp promoter respectively. These resulting plasmids are transformed into $E.\ coli$ MC1000 lambda lysogen or MM294, and the cells grown under non-inducing conditions and then induced by means appropriate to the promoter. The cells are harvested by centrifugation, sonicated and the liberated CSF-1 solubilized. The presence of human (or murine) CSF-1 is confirmed by subjecting the sonicate to the colony stimulating assay set forth above.

In addition, the plasmid pFC54.t (ATCC 39789) which contains the $P_L$ promoter and the Bacillis thuringiensis positive retroregulatory sequence (as described in EPO Application Publication No. 717,331, published 29 Mar. 1985) was used as a host vector. pFC54.5 was digested with HindIII/BamHI(blunt), and the desired coding sequences ligated into the vector using the HindIII/EcoRI(blunt) excised fragment from pcCSF-17 or the mutein encoding vectors described above. After transformation into E coli MC1000 lambda lysogen, and induction, CSF-1 production was obtained and verified as described above.

Finally, it was possible to improve the level of CSF-1 production from the foregoing constructs by altering the third nucleotide in each of the first six codons of the N-terminus. pFC54.5 containing the CSF-1 encoding fragment was digested with HindIII/BstXI, and the excised fragment (which contains the ATG and a short portion of the subsequent coding sequence) was replaced by a synthetic HindIII/BstXI segment wherein the first six codons have the sequence: GAAGAAGTTTCTGAATAT. The resulting analogous expression vector represents no change in the amino acid sequence encoded; however, the levels of expression are improved when this modified vector is used.

Eucaryotic Expression

The Okayama-Berg plasmid pcCSF-17, containing the cDNA encoding human CSF-1 under control of the SV40 promoter, can also be used to effect stable expression in monkey CV-1 cells, the parent cell line from which the COS-7 line was derived. The corresponding vectors encoding the muteins as described above can also be used in an exactly analogous way. The host monkey CV-1 cells were grown to confluence and then cotransformed using 10 µg pcCSF-17 and various amounts (1, 2, 5 and 10 µg) of pRSV-NEO2 (Gorman, C., et al, *Science* (1983) 221:551–553) per 500,000 cells. The transformants were grown in DMEM with 10% FBS medium containing 100 µg/ml of G418 antibiotic, to which the pRSV-NEO2 plasmid confers resistance. The CV-1 cell line showed a G418 transformation frequency of $10^{-5.12}$ colonies per $10^6$ cells per µg DNA.

The CV-1 cells were cotransformed as described above and selected in G418-containing medium. Resistant clones were tested for stability of the G418-resistant phenotype by growth in G418-free medium and then returned to G418-containing medium. The ability of these cultures to survive when returned to antibiotic-containing medium suggests that the pRSV-NEO2 DNA was integrated permanently into the cell genome. Since cells stably transformed with a marker plasmid have about 50% probability of having integrated the DNA of a cotransfecting plasmid, about half of these cells will also contain pcCSF-17 DNA in their chromosomal DNA.

Several clones of the G418-resistant pools of CV-1 cells which were demonstrated to be stably transformed as above were picked and grown in duplicate flasks to near confluence. One flask of each duplicate was infected with SV-40 virus at a multiplicity of infection of 5, and the medium was harvested 6 days after infection for assay for CSF-1 using a radioimmunoassay. The immunoassay is based on competition of $^{125}$I-labeled MIAPaCa CSF-1 for "Rabbit 52" polyclonal antiserum raised against purified human urinary CSF-1.

One of the selected CV-1 clones showed 2335 U/ml production of CSF-1, according to this assay, whereas cells not infected with SV-40 showed less than 20 U/ml. Controls using COS-7 cells transformed with 10 µg pcCSF-17 showed 2400 U/ml CSF-1 production without SV-40 infection.

The CSF-1 producing CV-1 cell line contains the pcCSF-17 DNA stably integrated into its genome, and thus can be used for stable production of CSF-1 upon infection with SV-40. Infection is presumed to "rescue" the pcCSF-17 DNA from the genome, and provide the SV-40 T-antigen necessary for replication of the rescued DNA. Without SV-40 infection, the integrated pcCSF-17 DNA is not effectively expressed.

Optimization of the expression of the CSF-1 encoding sequence by the CV-1 (CSF-17) cell line showed 6500–8000 U/ml when measured by the radioimmunoassay six days after SV-40 infection using a multiplicity of infection of at least 1, and a 10% FBS medium. Studies on expression levels at a multiplicity of 10 showed comparable production, but production was reduced upon removal of the FBS from the medium on the second day after infection.

In the alternative, appropriate control systems and host vectors permitting expression in eucaryotic hosts may be used to receive the CSF-1 encoding inserts. For example, CHO cells and suitable vectors may be used, as described in U.S. Ser. No. 438,991, filed 1 Nov. 1982, assigned to the same assignee and incorporated herein by reference.

E.6. Activity of CSF-1

Additional definition of the activity of CSF-1 was provided using partially purified MIAPaCa CSF-1 or murine L cell CSF-1 as models for the CV-1-produced recombinant material. CSF-1 was shown to enhance the production of interferon and tumor necrosis factor (TNF) by induced human monocytes by up to 10-fold. CSF-1 also was demonstrated to stimulate macrophage antitumor toxicity.

Stimulation of TNF Production by Human Monocytes

MIAPaCa CSF-1 was purified from the supernatant by calcium phosphate gel filtration and lentil lectin chromatography. For assay of lymphokine production, peripheral blood-adherent cells were incubated in duplicate flasks containing $10^7$ cells each. One flask was treated with 1000 U/ml CSF-1 purified as above. After 3 days, the cells were harvested, and washed, and resuspended at a cell concentration of $5\times10^5$/ml and plated in 24-well plates at 0.5 ml/well. The wells were treated with 10 µg/ml LPS and 20 ng/ml PMA for 48 hr and the supernatants were harvested for TNF assay. Cells treated with CBF showed TNF secretions approximately nine-fold higher than the untreated cells (1500 U/ml, compared to 162 U/ml).

Stimulation of Interferon Production by Human Monocytes

In an analogous experiment to determine the effect of CSF-1 on interferon production, peripheral blood-adherent cells were incubated for 3 days in the presence and absence of 1000 U/ml CSF-1, as described above, harvested, resuspended at $5\times10^5$/ml, and plated in a 25-well plate, as described above. The cells were induced for interferon production by addition of varying amounts of poly(I-):poly(C). The supernatants were assayed for interferon production by their cytopathic effect on VSV-infected GM 2504 cells. The CSF-1-stimulated cells showed production of 100 U/ml when induced with 50 μg/ml poly(I):poly(C), as described by McCormick, F., et al. *Mol Cell Biol* (1984) 4:166, whereas comparably induced untreated cells produced less than 3 U/ml.

Stimulation of Myeloid CSF Production by Human Monocytes

Monocytes were incubated ±CSF-1 for 3 days and then induced for production of myeloid CSF as in Table 1. The three representative experiments shown used blood from different donors.

TABLE 2

| | Myeloid CSF (U/ml) | | | | | |
|---|---|---|---|---|---|---|
| | Exp. 1 | | Exp. 2 | | Exp. 3 | |
| Induction | −CSF | +CSF | −CSF | +CSF | −CSF | +CSF |
| medium | 0 | 0 | 0 | 0 | 0 | 0 |
| 0.1 μg/ml LPS | — | — | 0 | 0 | 0 | 80 ± 17 |
| 1 μg/ml LPS | 0 | 700 ± 72 | 40 ± 20 | 200 ± 20 | 103 ± 12 | 377 ± 57 |
| 0.1 μg/ml LPS + 2 ng/ml PMA | — | — | 617 ± 50 | 993 ± 101 | 1120 ± 82 | 1280 ± 60 |
| 1 μg/ml LPS + 2 ng/ml PMA | 283 ± 42 | 983 ± 252 | 360 ± 92 | 1400 ± 180 | 537 ± 47 | 1080 ± 12 |
| 2 ng/ml PMA | — | 370 ± 17 | 297 ± 6 | 183 ± 15 | 380 ± 52 | 716 ± 76 |

Therefore, CSF-1 stimulates CBF-GM production.

Stimulation of Tumor Cell Killing by Murine Macrophage; Comparison to other Colony Stimulating Factors To assay macrophage stimulation, murine CSF-1 obtained from L-cell-conditioned medium, was used as a model for the recombinantly produced CSF-1 from pcCSF-17 in an assay which showed stimulation of the ability of murine macrophages to kill sarcoma targets. In this assay, normal 2 hr adherent C3HeN mouse peritoneal macrophages were incubated for 1 day in vitro with and without CSF-1 and then mixed at a 20:1 ratio with $^3$H-thymidine-labeled mouse sarcoma TU5 cells along with 10% v/v conA-induced (10 μg/ml) spleen lymphokine (LK), which contains gamma interferon. The release of labeled thymidine over the following 48 hr was used as a measure of tumor cell killing. The effect of adding CSF-1 as murine L-cell-conditioned medium containing 1200 U/ml CSF-1 is shown in the following table.

| Treatment | | Kill % | Increase Due to CSF-1 % |
|---|---|---|---|
| DAY 0→1 | DAY 1→3 | | |
| — | — | 13 | |
| — | LK | 39 | |
| — | CSF-1 + LK | 49 | 26 |
| CSF-1 | LK | 51 | 31 |
| CSF-1 | CSF-1 + LK | 60 | 54 |
| — | — | 3 | |
| — | LK | 35 | |
| — | CSF-1 + LK | 47 | 34 |
| CSF-1 | — | 7 | |
| CSF-1 | LK | 49 | 40 |
| CSF-1 | CSF-1 + LK | 69 | 97 |

Increase in the ability to kill the target cells was noted whether CSF-1 was added during the preliminary 1 day of growth or during the period of induction; however, the most dramatic effects were observed when CSF-1 was present during both of these periods.

The possibility of contaminating bacterial lipopolysaccharide (LPS) as the cause of stimulation of monocytes and macrophages was excluded: The LPS content of the applied CSF-1 was low (<0.3 ng/3000 U CSF-1, by Limulus amoebocyte lysate assay); activity was removed by application to an anti-CSF-1 column; polymyxin B was used to neutralize LPS; the macrophages from C3H/HeJ mice respond to CSF-1 but not to LPS.

CSF-GM was prepared from 6 mouse lungs obtained 5 hours after IV administration of 5 μg LPS. The lungs were chopped and incubated for 3 days in serum free medium, and the supernatant was depleted of CSF-1 using a YYG106 affinity column (CSF-1 content reduced from 270 U/ml to 78 U/ml). CSF-G was prepared from similarly treated LDI serum free medium. Both CSF-GM and CSF-G contents were assayed at 2000 U/ml by colony stimulating assay.

The peritoneal macrophages were incubated with 40% of either of the foregoing media or with L-cell medium assayed at 2000 U/ml CSF-1 for-1 day, and then incubated for 48 hours either with additional medium or with LK, and assayed for TU5 killing as described above.

The results are shown in FIG. 6. While CSF-1 showed marked enhancement of toxicity to TU5, neither CSF-G nor CSF-GM had any effect.

Stimulation of Murine Antiviral Activity

Adherent murine thioglycolate-elicited macrophages were incubated with CSF-1 for 3 days and infected with VSV overnight. Polymyxin B was added to test samples to block the LPS induction of interferon. The following table shows crystal violet staining of cells remaining adherent.

TABLE 3

| | Crystal Violet | |
|---|---|---|
| Treatment | −Polymyxin B (mean)(S.D.) | +Polymyxin B |
| Medium/No VSV | .158 ± .019 | |
| Medium + VSV | .0583 ± .02 | .049 ± .009 |
| CSF-1 625 U/ml + VSV | .139 ± .018 | .177 ± .04 |
| 1250 + VSV | .167 ± .06 | .205 ± .07 |
| 2500 + VSV | .160 ± .06 | .219 ± .04 |

TABLE 3-continued

| | Crystal Violet | |
|---|---|---|
| Treatment | −Polymyxin B (mean)(S.D.) | +Polymyxin B |
| 5000 + VSV | .150 ± .03 | .202 ± .06 |

CSF-1 treated cells, therefore, showed protection of the macrophage against VSV.

E.7 Formulation of CSF-1

The recombinantly produced human CSF-1 may be formulated for administration using standard pharmaceutical procedures. Ordinarily CSF-1 will be prepared in injectable form, and may be used either as the sole active ingredient, or in combination with other proteins or other compounds having complementary or similar activity. Such other compounds may include alternate antitumor agents such as adriamycin, or lymphokines, such as IL-1, -2, and -3, alpha-, beta-, and gamma-interferons and tumor necrosis factor. The effect of the CSF-1 active ingredient may be augmented or improved by the presence of such additional components. As described above, the CSF-1 may interact in beneficial ways with appropriate blood cells, and the compositions of the invention therefore include incubation mixtures of such cells with CSF-1, optionally in the presence of additional lymphokines. Either the supernatant fractions of such incubation mixtures, or the entire mixture containing the cells as well, may be used.

F. Murine CSF-1

An intronless DNA sequence encoding murine CSF-1 is prepared using a murine fibroblast cell line which produces large amounts of CSF-1. The L-929 line, obtainable from ATCC, is used as a source for mRNA in order to produce a cDNA library. Using oligomeric probes constructed on the basis of the known murine N-terminal and CNBr-cleaved internal peptide sequence, this cDNA library is probed to retrieve the entire coding sequence for the murine form of the protein. Murine CSF-1 is believed to be approximately 80% homologous to the human material because of the homology of the N-terminal sequences, the ability of both human and murine CSF-1 preparations to stimulate macrophage colonies from bone marrow cells, and limited cross-reactivity with respect to radioreceptor and radioimmunoassays (Das, S. K., et al, *Blood* (1981) 58:630).

F.1. Protein Purification

Murine CSF-1 was purified by standard methods similar to those that are disclosed by Stanley, E. R. et al, *J Immunol Meth* (1981) 42: 253–284 and by Wang, F. F., et al, *J Cell Biochem* (1983) 21:263–275 or SDS gel electrophoresis as reviewed by Hunkapiller, M. W., et al, *Science* (1984) 226:304.

Amino acids 1–39 of the murine sequence were obtained, taking advantage of cyanogen bromide cleavage at position 10 to extend the degradation procedure. An internal cleavage fragment from the mouse protein was also obtained and sequenced.

Overall composition data for the mouse protein were also obtained as shown below. These data show correct relative mole % for those amino acids showing good recoveries; however the numbers are not absolute, as histidine and cysteine were not recovered in good yield.

| Amino Acid | mole % | residues/125 |
|---|---|---|
| Asp | 20.1 | 25.1 |
| Glu | 20.0 | 25.0 |
| His | — | — |
| Ser | 6.0 | 7.5 |
| Thr | 5.9 | 7.4 |
| Gly | 5.4 | 6.8 |
| Ala | 6.8 | 8.5 |
| Arg | 3.0 | 3.8 |
| Pro | 6.7 | 8.4 |
| Val | 5.3 | 6.6 |
| Met | 1.1 | 1.4 |
| Ile | 3.9 | 4.9 |
| Leu | 8.5 | 10.6 |
| Phe | 6.0 | 7.5 |
| Lys | 3.5 | 4.4 |
| Tyr | 4.1 | 5.1 |

The conversion to residues/125 was based on an approximation of sequence length from molecular weight.

F.2. Preparation of Murine CSF-1 cDNA

The amino acid sequence 5–13 of the murine CSF-1 and the internal sequence were used as a basis for probe construction.

Three sets of oligomers corresponding to the murine sequence were prepared. One sequence was prepared to encode "region A"—i.e., amino acids 9–13; another was prepared to "region B"—i.e., amino acids 5–9, as shown in FIG. 2; a third, to encode positions 0–6 of an internal sequence, "region C". Because of codon redundancy, each of these classes of oligomers is highly degenerate.

Thus, 15-mers constructed on the basis of region A number 48; 14-mers constructed on the basis of region B (deleting the last nucleotide of the codon for histidine) also number 48; 20-mers constructed on the basis of region C number 32. Alternatively stated, a 15-mer constructed so as to encode region A may have a mismatch in four of the fifteen positions; a particular 14-mer constructed with respect to region B may have a mismatch in six positions; a particular 20-mer constructed with respect to region C may have a mismatch in five positions.

As described below, by suitable protocol design, an enriched messenger RNA fraction may be found for the production of the desired enriched murine cDNA library, and the precisely correct oligomers for use as probes also ascertained.

Total messenger RNA is extracted and purified from murine L-929 cells. Murine L-929 cells are cultured for 8 days on DME medium and then harvested by centrifugation. Total cytoplasmic ribonucleic acid (RNA) was isolated from the cells by the same protocol as set forth above for MIAPaCa mRNA.

The mRNA is fractionated on gels for Northern blot as described in paragraph C.3. The 15-mer sequences corresponding to region A are divided into four groups of twelve each. Each of these groups was used to hybridize under low stringency both to control and to murine L-929 mRNA slabs and the resulting patterns viewed by radioautography. Under the low stringency conditions employed, hybridization occurs to fractions not containing the proper sequence, as well as those that do. Also, because the control cell line is different from that of the L-929 line in ways other than failure to produce CSF-1, hybridization occurs in a number of size locations not related to CSF-1 in the L-929 cell gels which are not present in the controls.

Comparable sets of control and L-929 gels are probed with segregants of the 48 14-mers representing region B and segregants of the 32 20-mers representing region C. Only the bands of messenger RNA which hybridize exclusively in the L-929 slabs for either regions A or B, and C probes are then further considered.

The RNA band which continues to bind to one of the A region 15-mer mixture or one of the region B 14-mer mixture and one of the region C 20-mer mixture under conditions of increasingly higher stringency is selected.

When the correct mRNA band is found, each of the groups of region A 15-mers is used to probe at various stringency conditions. The group binding at highest stringency presumably contains the correct 15-mer exactly to complement the mRNA produced. The correct 15-mer is ascertained by further splitting the preparation until a single oligomer is found which binds at the highest stringency. A similar approach is used to ascertain the correct 14-mer or 20-mer which binds to region B or C. These specific oligomers are then available as probes in a murine cDNA library which is prepared from the enriched mRNA fraction.

The mRNA fraction identified as containing the coding sequence for CSF-1 is then obtained on a preparative scale. In this preparation, the poly $A^+$ mRNA was fractionated on a sucrose gradient in 10 mM Tris-HCl, pH 7.4, 1 mM EDTA, and 0.5% SDS. After centrifugation in a Beckman SW40 rotor at 30,000 rpm for 17 hr, mRNA fractions are recovered from the gradient by ethanol precipitation. RNA fractions recovered from the gradient were each injected into Xenopus oocytes in a standard translation assay and the products assayed for CSF-1 using radioimmunoassay with antibodies raised against murine CSF-1. Fractions for which positive results were obtained were pooled and used to construct the cDNA library. These same fractions hybridize to the oligomeric probes.

Other methods of preparing cDNA libraries are, of course, well known in the art. One, now classical, method uses oligo dT primer, reverse transcriptase, tailing of the double stranded cDNA with poly dG, and annealing into a suitable vector, such as pBR322 or a derivative thereof, which has been cleaved at the desired restriction site and tailed with poly dC. A detailed description of this alternate method is found, for example, in U.S. Ser. No. 564,224, filed 20 Dec. 1983, and assigned to the same assignee, incorporated herein by reference.

In the method used here, the enriched mRNA (5 µg) is denatured by treatment with 10 mM methyl mercury at 22° C. for 5 min and detoxified by the addition of 100 mM 2-mercaptoethanol (Payvar, F., et al, *J Biol Chem* (1979) 254:7636–7642). Plasmid pcDV1 is cleaved with KpnI, tailed with dTTP, and annealed to the denatured mRNA. This oligo dT primed mRNA is treated with reverse transcriptase, and the newly synthesized DNA strand tailed with dCTP. Finally, the unwanted portion of the pcDV1 vector is removed by cleavage with HindIII. Separately, pL1 is cleaved with PstI, tailed with dGTP, cleaved with HindIII, and then mixed with the poly T tailed mRNA/cDNA complex extended by the pcDV1 vector fragment, ligated with *E. coli* ligase and the mixture treated with DNA polymerase I (Klenow) *E. coli* ligase, and RNase H. The resulting vectors are transformed into *E. coli* K12 MM294 to $Amp^R$.

The resulting cDNA library is then screened using the oligomer probes identified as complementary to the mRNA coding sequence as described above. Colonies hybridizing to probes from regions A or B and C are picked and grown; plasmid DNA isolated, and plasmids containing inserts of sufficient size to encode the entire sequence of CSF-1 isolated. The sequence of the insert of each of these plasmids is determined, and a plasmid preparation containing the entire coding sequence including regions A and B at the upstream portion is designated pcMCSF.

F.3 Expression of Murine CSF-1 DNA

In a manner similar to that set forth above for the human cDNA, the murine cDNA is tested for transient expression in COS cells, and used for expression in stably transformed CV-1. In addition, the appropriate HindIII/ATG encoding sequences are inserted upstream of the mature protein by mutagenesis and the coding sequences inserted into pPLOP or pTRP3 for procaryotic expression.

G. Host Vectors pPLOP is a host expression vector having the $P_L$ promoter and N gene ribosome binding site adjacent a HindIII restriction cleavage site, thus permitting convenient insertion of a coding sequence having an ATG start codon preceded by a HindIII site. The backbone of this vector is a temperature-sensitive high copy number plasmid derived from pCS3. pPLOP was deposited at ATCC on 18 Dec. 1984, and has accession number 39947.

pTRP3 is a host expression vector containing a trp promoter immediately upstream of a HindIII restriction site, thus permitting insertion of a coding sequence in a manner analogous to that above for pPLOP. The backbone vector for pTRP3 is pBR322. pTRP3 was deposited with ATCC on 18 Dec. 1984, and has accession number 39946.

Construction of pPLOP

Origin of Replication pCS3 provides an origin of replication which confers high copy number of the pPLOp host vector at high temperatures. Its construction is described extensively in U.S. Ser. No. 541,948, filed 14 Oct. 1983, incorporated herein by reference. pCS3 was deposited 3 Jun. 1982 and assigned ATCC number 39142.

pCS3 is derived from pEW27 and pOP9. pEW27 is described by E. M. Wong, *Proc Natl Acad Sci (USA)* (1982) 79:3570. It contains mutations near its origin of replication which provide for temperature regulation of copy number. As a result of these mutations replication occurs in high copy number at high temperatures, but at low copy number at lower temperatures.

pOP9 is a high copy number plasmid at all temperatures which was constructed by inserting into pBR322 the EcoRI/PvuII origin containing fragment from Col E1 type plasmid pOP6 (Gelfand, D., et al, *Proc Natl Acad Sci (USA)* (1978) 75:5869). Before insertion, this fragment was modified as follows: 50 µg of pOP6 was digested to completion with 20 units each BamHI and SstI. In order to eliminate the SstI 3' protruding ends and "fill in" the BamHI 5' ends, the digested pOP6 DNA was treated with *E. coli* DNA polymerase I (Klenow in a two-stage reaction first at 20° C. for elimination of the 3' SstI protruding end and then at 9° C. for repair at the 5' end. The blunt ended fragment was digested and 0.02 pmole used to transform competent DG75 (O'Farrell, P., et al, *J Bacteriology* (1978) 134:645–654). Transformants were selected on L plates containing 50 µ/ml ampicillin and screened for a 3.3 kb deletion, loss of an SstI site, and presence of a newly formed BamHI site.

One candidate, designated pOP7, was chosen and the BamHI site deleted by digesting 25 μg of pOP7 with 20 units BamHI, repairing with *E. coli* DNA polymerase I fragment (Klenow), and religating with T4 DNA ligase. Competent DG75 was treated with 0.1 μg of the DNA and transformants selected on L plates containing 50 μg/ml ampicillin. Candidates were screened for the loss of the BamHI restriction site. pOP8 was selected. To obtain pOP9 the AvaI(repaired)/EcoRI Tet$^R$ fragment from pBR322 was prepared and isolated and ligated to the isolated PvuII(partial)/EcoRI 3560 bp fragment from pOP8.

Ligation of 1.42 kb EcoRI/AvaI(repair) Tet$^R$ (fragment A) and 3.56 kb EcoRI/PvuII Amp$^R$ (fragment B) used 0.5 μg of fragment B and 4.5 μg of fragment A in a two-stage reaction in order to favor intermolecular ligation of the EcoRI ends.

Competent DG75 was transformed with 5 μl of the ligation mixture, and transformants were selected on ampicillin (50 μg/ml) containing plates. pOP9, isolated from Amp$^R$ Tet$^R$ transformants, showed high copy number, colicin resistance, single restriction sites for EcoRI, BamHI, PvuII, HindIII, 2 restriction sites for HincII, and the appropriate size and HaeIII digestion pattern.

To obtain pCS3, 50 μg pEW27 DNA was digested to completion with PvuII and the EcoRI. Similarly, 50 μg of pOP9 was digested to completion with PvuII and EcoRI and the 3.3 kb fragment was isolated.

0.36 μg (0.327 pmoles) pEW27 fragment and 0.35 μg (0.16 pmoles) pOP9 fragment were ligated and used to transform *E. coli* MM294. Amp$^R$ Tet$^R$ transformants were selected. Successful colonies were initially screened at 30° C. and 41° C. on beta-lactamase assay plate and then for plasmid DNA levels following growth at 30° C. and 41° C. A successful candidate, designated pCS3, was confirmed by sequencing.

Preparation of the P$_L$N$_{RBS}$ Insert

The DNA sequence containing P$_L$ phage promoter and the ribosome binding site for the N-gene (N$_{RBS}$) was obtained from pFC5, and ultimately from a derivative of pKC30 described by Shimatake and Rosenberg, *Nature* (1981) 292:128. pKC30 contains a 2.34 kb fragment from lambda phage cloned into the HindIII/BamHI vector fragment from pBR322. The P$_L$ promoter and N$_{RBS}$ occupy a segment in pKC30 between a BglII and HpaI site. The derivative of pKC30 has the BglII site converted to an EcoRI site.

The BglII site immediately preceding the P$_L$ promoter was converted into an EcoRI site as follows: pKC30 was digested with BglII, repaired with Klenow and dNTPs and ligated with T4 ligase to an EcoRI linker (available from New England Biolabs) and transformed into *E. coli* K12 strain MM294 lambda$^+$. Plasmids were isolated from Amp$^R$ Tet$^R$ transformants and the desired sequence confirmed by restriction analysis and sequencing. The resulting plasmid, pFC3, was double-digested with PvuI and HpaI to obtain an approximately 540 bp fragment isolated and treated with Klenow and dATP, followed by S1 nuclease, to generate a blunt ended fragment with the 3' terminal sequence -AG-GAGAA where the -AGGAGA portion is the N$_{RBS}$. This fragment was restricted with EcoRI to give a 347 base pair DNA fragment with 5'-EcoRI (sticky) and HinfI (partial repair, S1 blunt)-3' termini.

To complete pFC5, pβI-Z15 was used to create a HindIII site 3' of the N$_{RBS}$. pβI-Z15 was deposited 13 Jan. 1984, ATCC No. 39578, and was prepared by fusing a sequence containing ATG plus 140 bp of β-IFN fused to lac Z into pBR322. In pβI-Z15, the EcoRI site of pBR322 is retained, and the insert contains a HindIII site immediately preceding the ATG start codon of β-IFN. pβI-Z15 was restricted with HindIII, repaired with Klenow and dNTPs, and then digested with EcoRI. The resulting EcoRI/HindIII (repaired) vector fragment was ligated with the EcoRI/HinfI (repaired) fragment above, and the ligation mixture used to transform MC1000-39531. Transformants containing the successful construction were identified by ability to grow on lactose minimal plates at 34° but not at 30°. (Transformations were plated on X-gal-Amp plates at 30° and 34° and minimal-lactose plates at 30° and 34°. Transformants with the proper construction are blue on X-gal-Amp plates at both temperatures, but on minimal lactose plates, grow only at 34°.) The successful construct was designated pFC5.

Completion of pPLOP pCS3 was then modified to provide the P$_L$ and N$_{RBS}$ control sequences. pCS3 was digested with HindIII, and then digested with EcoRI. The vector fragment was ligated with an isolated EcoRI/HindIII from pFC5 containing the P$_L$N$_{RBS}$ and transformed into *E. coli* MM294. The correct construction of isolated plasmid DNA was confirmed by restriction analysis and sequencing and the plasmid designated pPLOP.

Preparation of pTRP3

To construct the host vector containing the trp control sequences behind a HindIII site, the trp promoter/operator/ribosome, binding site sequence, lacking the attenuator region, was obtained from pVH153, obtained from C. Yanofsky, Stanford University. Trp sequences are available in a variety of such plasmids known in the art. pVH153 was treated with HhaI (which cuts leaving an exposed 3' sticky end just 5' of the trp promoter) blunt ended with Klenow, and partially digested with TagI. The 99 bp fragment corresponding to restriction at the TagI site, 6 nucleotides preceding the ATG start codon of trp leader, were isolated, and then ligated to EcoRI (repair)/ClaI digested, pBR322 to provide pTRP3.

On 2 Apr. 1985, Applicants have deposited with the American Type Culture Collection, Rockville, Md., USA (ATCC) the phage pHCSF-1 in *E. coli* DG98, accession no. 40177. On 21 May 1985, pHCSF-1a, designated CMCC 2312 in the Cetus collection and pHCSF-1 λ Charon 4A for deposit, was deposited with ATCC and has accession no. 40185. On 14 Jun. 1985, C8F-17 in *E coli* MM294, designated CMCC 2347, was deposited with ATCC and has accession no. 53149. In addition, the following deposits were made with ATCC on the date of 19 Jun. 1986:

| Plasmid | CMCC No. | ATCC No. |
| --- | --- | --- |
| pCSF-asp59 | 2705 | 67139 |
| pCSF-gln52 | 2708 | 67140 |
| pCSF-pro52 | 2709 | 67141 |
| pCSF-Bam | 2710 | 67142 |
| pCSF-BamBcl | 2712 | 67144 |
| pCSF-Gly150 | 2762 | |

These deposits were made under the provisions of the Budapest Treaty on the International Recognition of the Deposit of Microorganisms for the Purposes of Patent Procedure and the Regulations thereunder (Budapest Treaty).

This assures maintenance of a viable culture for 30 years from date of deposit. The deposits will be made available by ATCC under the terms of the Budapest Treaty, and subject to an agreement between Applicants and ATCC which assures permanent and unrestricted availability upon issuance of the pertinent US patent. The Assignee herein agrees that if the culture on deposit should die or be lost or destroyed when cultivated under suitable conditions, it will be promptly replaced upon notification with a viable specimen of the same culture. Availability of the deposits is not to be construed as a license to practice the invention in contravention of the rights granted under the authority of any government in accordance with its patent laws.

These deposits were made for the convenience of the relevant public and do not constitute an admission that a written description would not be sufficient to permit practice of the invention or an intention to limit the invention to these specific constructs. Set forth hereinabove is a complete written description enabling a practitioner of ordinary skill to duplicate the constructs deposited and to construct alternative forms of DNA, or organisms containing it, which permit practice of the invention as claimed.

The scope of the invention is not to be construed as limited by the illustrative embodiments set forth herein, but is to be determined in accordance with the appended claims.

We claim:

1. A purified, homogeneous, recombinant, non-glycosylated human CSF-1 protein preparation that is substantially free from other human proteins, wherein said protein, in its active form, is capable of stimulating the formation of primarily macrophage colonies in a standard in vitro CSF-1 assay consisting of the amino acid sequence set out in FIGS. 5-1 and 5-2 from position 1 to position 158.

2. A purified, homogeneous, recombinant human CSF-1 protein preparation in accordance with claim 1, wherein the protein has the amino acid sequence set out in FIGS. 5-1 and 5-2 from position 1 to position 150.

3. A purified, homogeneous, recombinant human CSF-1 protein preparation in accordance with claim 1, wherein the lysine residue is replaced with a different amino acid at positions selected from the group consisting of residues 51 or 52.

4. A purified, homogeneous, recombinant human CSF-1 protein preparation in accordance with claim 2, wherein the lysine residue is replaced with a different amino acid at positions selected from the group consisting of residues 51 or 52.

5. A pharmaceutical composition comprising the protein of claim 1 and a pharmaceutically acceptable excipient.

6. A pharmaceutical composition comprising the protein of claim 2 and a pharmaceutically acceptable excipient.

7. A pharmaceutical composition in accordance with claim 6 further comprising a pharmaceutically acceptable excipient selected from the group consisting of Ringer's solution, Hank's solution, water, saline, glycerol and dextrose.

8. A purified, homogeneous, recombinant human CSF-1 protein preparation in accordance with claim 1, wherein the sequence is encoded by DNA selected from the group consisting of pCSF-Bam, pCSF-BamBcl, pCSF-Bam TGA and pCSF-Gly150.

* * * * *